US010369003B2

(12) United States Patent
Moskowitz et al.

(10) Patent No.: US 10,369,003 B2
(45) Date of Patent: Aug. 6, 2019

(54) ARTIFICIAL CERVICAL AND LUMBAR DISCS, DISC PLATE INSERTION GUN FOR PERFORMING SEQUENTIAL SINGLE PLATE INTERVERTEBRAL IMPLANTATION ENABLING SYMMETRIC BI-DISC PLATE ALIGNMENT FOR INTERPLATE MOBILE CORE PLACEMENT

(71) Applicant: Moskowitz Family LLC, Rockville, MD (US)

(72) Inventors: Nathan C. Moskowitz, Rockville, MD (US); Mosheh T. Moskowitz, Rockville, MD (US); Ahmnon D. Moskowitz, Rockville, MD (US); Pablo A. Valdivia Y. Alvarado, Cambridge, MA (US)

(73) Assignee: Moskowitz Family LLC, Rockville, MD (US)

( * ) Notice: Subject to any disclaimer, the term of this patent is extended or adjusted under 35 U.S.C. 154(b) by 0 days.

(21) Appl. No.: 16/018,798

(22) Filed: Jun. 26, 2018

(65) Prior Publication Data
US 2018/0368985 A1 Dec. 27, 2018

Related U.S. Application Data

(63) Continuation of application No. 15/944,221, filed on Apr. 3, 2018, which is a continuation of application
(Continued)

(51) Int. Cl.
*A61F 2/44* (2006.01)
*A61F 2/46* (2006.01)
*A61F 2/30* (2006.01)

(52) U.S. Cl.
CPC ............ *A61F 2/442* (2013.01); *A61F 2/4425* (2013.01); *A61F 2/4611* (2013.01);
(Continued)

(58) Field of Classification Search
None
See application file for complete search history.

(56) References Cited

U.S. PATENT DOCUMENTS 4,554,914 A 11/1985 Kapp et al.
4,636,217 A 1/1987 Ogilvie et al.
(Continued)

FOREIGN PATENT DOCUMENTS

WO   WO 2004/041129   5/2004

OTHER PUBLICATIONS

Vincent C. Traynelis, "Prosthetics and Biologics: The Wave of the Future," Clinical Neurosurgery, vol. 50, Proceedings of the Congress of Neurological Surgeons, Philadelphia, PA 2002, Chapter 9, pp. 207-219.
(Continued)

*Primary Examiner* — Sameh R Boles
(74) *Attorney, Agent, or Firm* — Fish & Richardson P.C.

(57) ABSTRACT

An artificial replacement disc includes a pair of substantially parallel plates formed to occupy a space defined by vertebral endplates, each of the plates including a plurality of spikes on a first surface and a concave trough formed on a second surface opposite of the first surface. A mobile core includes a core rim with opposing convex surfaces extending from opposite sides of the core rim, the mobile core being capable of being disposed between the pair of plates to permit the vertebral endplates to move relative to one another. The spikes on each of the plates extend substantially away from the mobile core and the convex surfaces are formed to integrally fit within the concave trough of at least one of the plates. The core rim limits lateral movement of the mobile core relative to the parallel plates. One or more insertion tools for inserting and implanting the replacement disc are also described.

17 Claims, 38 Drawing Sheets

Related U.S. Application Data

No. 15/870,406, filed on Jan. 12, 2018, which is a continuation of application No. 14/739,327, filed on Jun. 15, 2015, now Pat. No. 9,867,712, which is a continuation of application No. 13/893,326, filed on May 13, 2013, now Pat. No. 9,056,018, which is a continuation of application No. 11/943,334, filed on Nov. 20, 2007, now Pat. No. 8,535,379, which is a continuation-in-part of application No. 11/487,415, filed on Jul. 17, 2006, now Pat. No. 7,854,766, and a continuation-in-part of application No. 11/019,351, filed on Dec. 23, 2004, now Pat. No. 7,083,650, said application No. 11/487,415 is a continuation-in-part of application No. 11/019,351, filed on Dec. 23, 2004, now Pat. No. 7,083,650, which is a continuation-in-part of application No. 10/964,633, filed on Oct. 15, 2004, now abandoned.

(60) Provisional application No. 60/788,720, filed on Apr. 4, 2006, provisional application No. 60/578,319, filed on Jun. 10, 2004, provisional application No. 60/573,346, filed on May 24, 2004, provisional application No. 60/572,468, filed on May 20, 2004, provisional application No. 60/570,837, filed on May 14, 2004, provisional application No. 60/570,098, filed on May 12, 2004.

(52) U.S. Cl.
CPC ............ *A61F 2002/30125* (2013.01); *A61F 2002/30604* (2013.01); *A61F 2002/30649* (2013.01); *A61F 2002/30662* (2013.01); *A61F 2002/30841* (2013.01); *A61F 2002/443* (2013.01); *A61F 2230/0008* (2013.01); *A61F 2230/008* (2013.01)

(56) References Cited

U.S. PATENT DOCUMENTS

| | | | |
|---|---|---|---|
| 4,759,766 A | 7/1988 | Buettner-Janz et al. | |
| 4,960,420 A | 10/1990 | Goble et al. | |
| 4,997,432 A * | 3/1991 | Keller ............... | A61B 17/025 600/219 |
| 5,123,926 A | 6/1992 | Pisharodi | |
| 5,314,477 A | 5/1994 | Marnay | |
| 5,401,269 A | 3/1995 | Buettner-Janz et al. | |
| 5,514,180 A | 5/1996 | Heggeness et al. | |
| 5,660,188 A | 8/1997 | Groiso | |
| 5,667,472 A | 9/1997 | Finn et al. | |
| 5,782,832 A | 7/1998 | Larsen et al. | |
| 5,960,522 A | 10/1999 | Boe | |
| 6,113,637 A | 9/2000 | Gill et al. | |
| 6,126,689 A | 10/2000 | Brett | |
| 6,368,350 B1 | 4/2002 | Erickson et al. | |
| 6,375,682 B1 | 4/2002 | Fleischmann et al. | |
| 6,419,704 B1 | 7/2002 | Ferree | |
| 6,458,159 B1 | 10/2002 | Thalgott | |
| 6,527,804 B1 | 3/2003 | Gauchet et al. | |
| 6,533,818 B1 | 3/2003 | Weber et al. | |
| 6,540,785 B1 | 4/2003 | Gill et al. | |
| 6,572,653 B1 | 6/2003 | Simonson | |
| 6,579,318 B2 | 6/2003 | Varga et al. | |
| 6,582,468 B1 | 6/2003 | Gauchet | |
| 6,610,093 B1 | 8/2003 | Pisharodi | |
| 6,641,614 B1 | 11/2003 | Wagner et al. | |
| 6,719,794 B2 | 4/2004 | Gelber | |
| 6,723,126 B1 | 4/2004 | Berry | |
| 6,730,088 B2 | 5/2004 | Yeh | |
| 6,733,532 B1 | 5/2004 | Gauchet et al. | |
| 6,764,491 B2 | 7/2004 | Frey et al. | |
| 6,770,094 B2 | 8/2004 | Fehling et al. | |
| 6,899,735 B2 | 5/2005 | Coates et al. | |
| 6,904,308 B2 | 6/2005 | Frisch et al. | |
| 6,908,484 B2 | 6/2005 | Zubok et al. | |
| 6,955,671 B2 | 10/2005 | Uchikubo | |
| 7,030,904 B2 | 4/2006 | Adair et al. | |
| 7,037,258 B2 | 5/2006 | Chatenever et al. | |
| 7,097,615 B2 | 8/2006 | Banik et al. | |
| 7,115,144 B2 | 10/2006 | Diaz et al. | |
| 7,118,580 B1 | 10/2006 | Beyersdorff et al. | |
| 7,250,060 B2 | 7/2007 | Trieu | |
| 7,927,373 B2 | 4/2011 | Parsons et al. | |
| 2004/0088054 A1 | 5/2004 | Berry | |
| 2004/0177531 A1 | 9/2004 | DiBenedetto et al. | |
| 2004/0254644 A1 | 12/2004 | Taylor | |
| 2005/0027362 A1 | 2/2005 | Williams et al. | |
| 2005/0049590 A1 | 3/2005 | Alleyne et al. | |
| 2005/0085910 A1 | 4/2005 | Sweeney | |
| 2005/0216084 A1 | 9/2005 | Fleischmann et al. | |
| 2005/0273170 A1 | 12/2005 | Navarro et al. | |
| 2005/0273174 A1 | 12/2005 | Gordon et al. | |
| 2005/0278026 A1 | 12/2005 | Gordon et al. | |
| 2006/0036325 A1 | 2/2006 | Paul et al. | |
| 2006/0155377 A1 | 7/2006 | Beaurain et al. | |
| 2006/0178745 A1 | 8/2006 | Bartish et al. | |
| 2006/0195192 A1 | 8/2006 | Gordon et al. | |
| 2007/0010826 A1 | 1/2007 | Rhoda et al. | |
| 2007/0055378 A1 | 3/2007 | Ankney et al. | |
| 2007/0073400 A1 | 3/2007 | Paul | |
| 2007/0198089 A1 | 8/2007 | Moskowitz et al. | |
| 2009/0204219 A1 | 8/2009 | Beaurain et al. | |

OTHER PUBLICATIONS

E.K. Wai et al., "Disk Replacement Arthroplasties: Can the Success of Hip and Knee Replacements be Repeated in the Spine?," Seminars in Spine Surgery, vol. 15, No. 4 Dec. 2003, pp. 4 73-482.

Richard D. Guyer et al., "lntervertebral Disc Prostheses," Spine Journal, vol. 28, No. 15S, Supp. To Aug. 1, 2003, pp. S15-S23.

Dieter Grob et al., "Clinical Ex~erience With the Dynesys Semi-rigid Fixation System for the Lumbar Spine," Spine, vol. 30, No. 3, 2005, pp. 24-331.

International Search Report (ISR) and Written Opinion of the International Searching Authority, Dec. 3, 2007, International Application No. PCT/US 07/05005.

\* cited by examiner

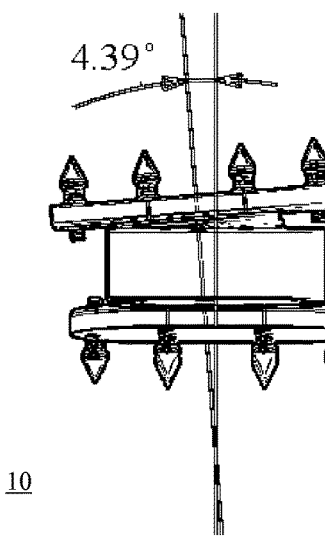 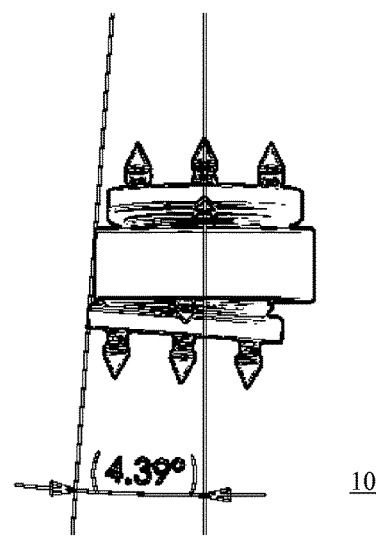
Figure 4Bi                Figure 4Bii

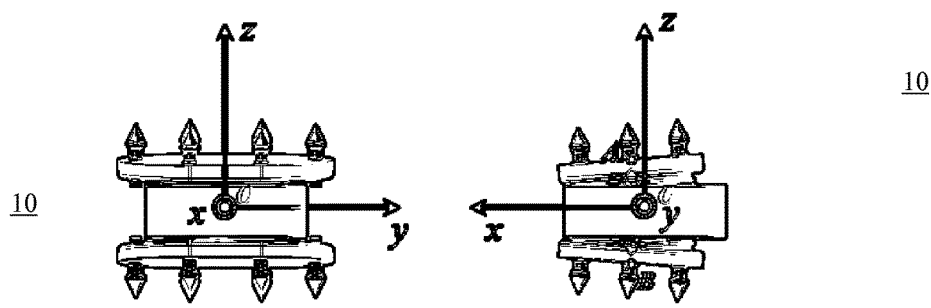
Figure 4Ci: Front View
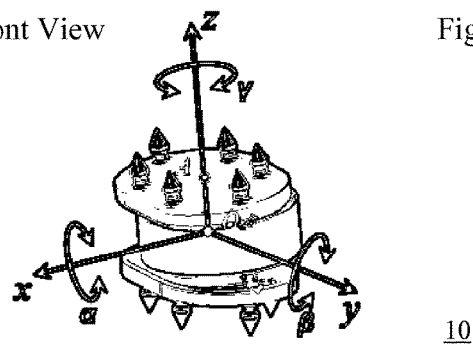
Figure 4Cii: Side View
Figure 4Ciii: Perspective View from Front-Side

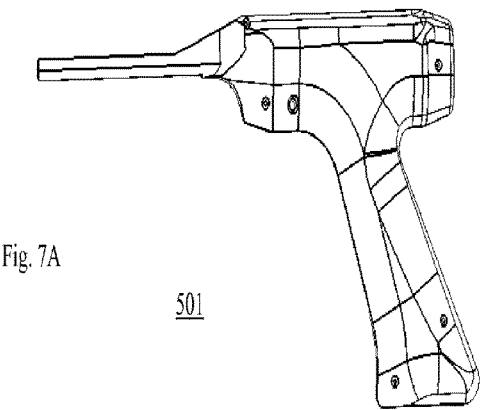
Fig. 7A 501
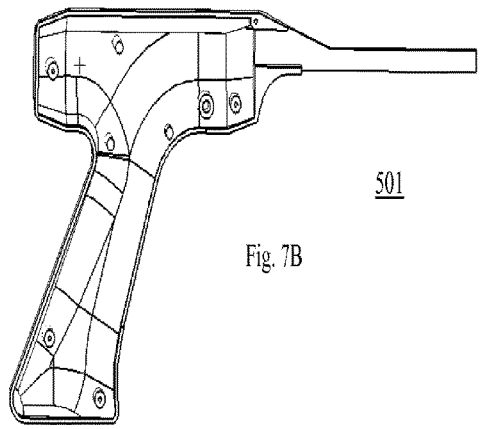
501 Fig. 7B
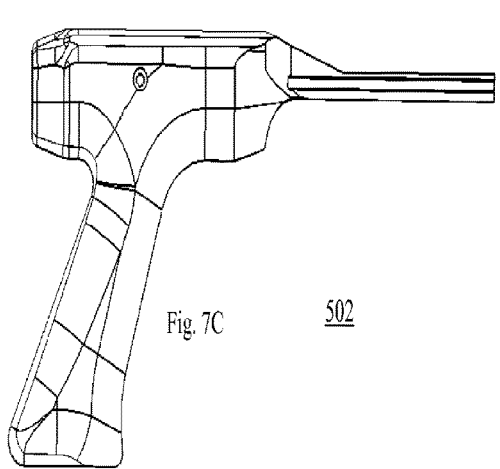
Fig. 7C 502
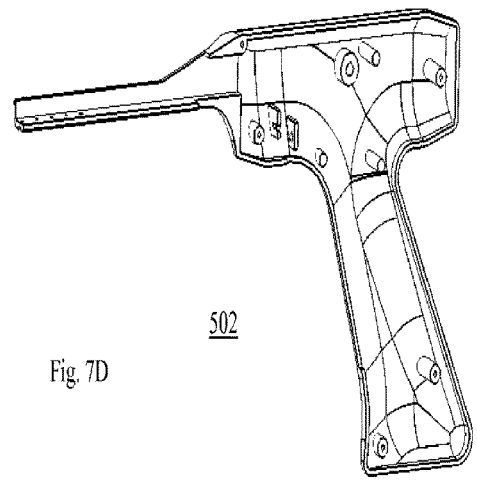
502 Fig. 7D

553

575

510

ARTIFICIAL CERVICAL AND LUMBAR DISCS, DISC PLATE INSERTION GUN FOR PERFORMING SEQUENTIAL SINGLE PLATE INTERVERTEBRAL IMPLANTATION ENABLING SYMMETRIC BI-DISC PLATE ALIGNMENT FOR INTERPLATE MOBILE CORE PLACEMENT

CROSS-REFERENCE TO RELATED APPLICATIONS

This application is a Continuation of U.S. application Ser. No. 15/944,221, filed Apr. 3, 2018, which is a Continuation of U.S. application Ser. No. 15/870,406, filed Jan. 12, 2018, which is a Continuation of U.S. application Ser. No. 14/739,327, filed Jun. 15, 2015 (now U.S. Pat. No. 9,867,712), which is a Continuation of U.S. application Ser. No. 13/893,326, filed May 13, 2013 (now U.S. Pat. No. 9,056,018), which is a Continuation of U.S. application Ser. No. 11/943,334, filed Nov. 20, 2007 (now U.S. Pat. No. 8,535,379), which is a Continuation in Part of U.S. application Ser. No. 11/487,415, filed Jul. 17, 2006, (now U.S. Pat. No. 7,854,766), and a Continuation in Part of U.S. application Ser. No. 11/019,351, filed Dec. 23, 2004 (now U.S. Pat. No. 7,083,650). The entire contents of all of the above identified patent applications are hereby incorporated by reference.

U.S. application Ser. No. 11/487,415 claims priority to 60/788,720, filed Apr. 4, 2006 and is a Continuation in Part of Ser. No. 11/019,351, filed Dec. 23, 2004 (now U.S. Pat. No. 7,083,650).

U.S. application Ser. No. 11/019,351 is a Continuation in Part of Ser. No. 10/964,633, filed Oct. 15, 2004, which claims priority to U.S. Application Nos. 60/570,098, filed May 12, 2004; 60/570,837, filed May 14, 2004; 60/572,468, filed May 20, 2004; 60/573,346, filed May 24, 2004; and 60/578,319, filed Jun. 10, 2004. The entire contents of all of the above identified patent applications are hereby incorporated by reference.

BACKGROUND

This description relates to a three piece mechanical total cervical artificial disc, which includes two spiked cervical plates and a mobile core. The disc may be inserted into the cervical intervertebral disc space using a novel disc plate insertion gun which performs sequential single plate intervertebral implantation enabling symmetric bi-disc plate alignment for inter plate mobile core placement. This cervical disc design and method of implantation avoid the cumbersome and arduous implantation techniques of many other artificial cervical disc designs improving safety, improving bone-plate insertion/integration, allowing multiple-level disc placement, preserving vertebral body integrity, eliminating the need for excessive disc space distraction, and decreasing procedure length. This description also relates to a modified application of the disc plate inserter design from copending, related applications describing posterior placed total artificial disc (PTTLAD). The modified disc plate inserter allows posterior lumbar sequential placement of two opposing disc plates rather than simultaneous two disc plate placement as outlined in our previous publication. The modified disc plate inserter enables implantation of the PTTLAD into narrower lumbar disc spaces which were not accessible with our previous lumbar disc plate inserter.

Cervical and lumbar discs are entering the clinical neurosurgical and orthopedic markets. The benefits of these artificial discs are well known and have been thoroughly reviewed in our prior and co-pending prosthetic disc patents, including Provisional Application 60/788,720 filed on Apr. 4, 2006, copending U.S. patent application Ser. No. 11/019,351, filed on Dec. 23, 2004 and Ser. No. 10/964,633, filed on Oct. 15, 2004, U.S. Provisional Application Nos. 60/578,319 filed on Jun. 10, 2004, 60/573,346 filed on May 24, 2004, 60/572,468 filed on May 20, 2004, 60/570,837 filed on May 14, 2004, and 60/570,098 filed on May 12, 2004, and U.S. patent application Ser. No. 11/487,415 filed on Jul. 17, 2006, the entire contents of each of which are hereby incorporated by reference. In one or more of the foregoing applications, we described four different cervical artificial disc embodiments which expanded in two or three-dimensions. This description presents an evolutionary simplification of these embodiments, e.g., with fewer small parts, which expand in only one dimension, and can be inserted very simply and efficiently. Accordingly, the advanced cervical disc design of the present application is a geometric modification of previous lumbar disc designs in one or more of the above-referenced patents, e.g., U.S. Patent Publication No. 2007/0198089 A1.

The cervical disc design of the present application differs from approaches of the background art which typically describe two-piece designs, e.g., as opposed to the three disc designs of the present application. In the two-piece designs, one piece consists of either an upper or lower cervical disc plate with a central trough to accommodate the opposing disc plate. The other piece, the opposing disc plate, has an incorporated dome shaped immobile core. The immobilized core is stationary and does not move. Semi-constrained artificial motion occurs as a result of the troughed plate movement against and around the immobilized core.

One or more of these designs are described in the following exemplary patent documents, including U.S. Pat. No. 5,314,477, filed Mar. 4, 1991 (Thierry Marnay), entitled "Prosthesis for intervertebral discs and instruments for implanting it;" U.S. Pat. No. 6,113,637 (Gill et al.), filed Oct. 22, 1998, entitled "Artificial intervertebral joint permitting translational and rotational motion; U.S. Pat. No. 6,540,785 B1 (Gill et al.) filed on Mar. 24, 2000, entitled "Artificial intervertebral joint permitting translational and rotational motion;" U.S. Pat. No. 6,8899,735 B2 (Bradley J Coates et. al.) filed on Oct. 2, 2002, entitled "Modular intervertebral prosthesis system," U.S. Pat. No. 6,908,484 B2 (Zubok et. al.) filed on Mar. 6, 2003, entitled "Cervical disc replacement." In each of the foregoing two-piece designs of the background art, the artificial implant is implanted within the vertebral bodies either by using attached hinges, keels or some form of extension which accommodates placement of vertebral screws.

The present inventors have determined that one disadvantage of most of these systems is that placement of the prosthesis is arduous, and time consuming, and can destroy a substantial part of the vertebral body after insertion of the device. The designs that use screws have the potential risks of screw pull out and secondarily esophageal injury, screw breakage, and/or inability to perform multilevel disc placement. Furthermore the fact that these designs do not have a mobile core leads to substantially constrained motion.

Similarly, U.S. Patent Publication No. 2007/0173936 A1 (Hester) filed on Jan. 23, 2006, describes a design which includes spikes, also includes a two-piece design with an immobilized core. One or more embodiments of the present application includes a mobile core which more closely simulates natural semi-constrained motion of a healthy cervical disc. U.S. Patent Publication No. 2005/0021146 A1

(de Villiers et al.) filed May 26, 2004 consists of two separate plates placed which are inserted simultaneously as one unit, after which a mobile core is inserted in between the plates. However, the plates include keels which can damage vertebral bodies, and prevent multilevel placement. U.S. Pat. No. 6,001,130 (Bryan), filed Oct. 6, 1997, describes a one piece design. However, the one-piece design involves an arduous placement technique involving disc space distraction, and the use of hinges and screws, limiting multi-level placement.

SUMMARY

One or more of the embodiments of the present application overcome one or more of the above-described shortcomings of the background art. For example, a cervical disc design and tool for implantation of the cervical disc is an improvement over one or more of the above mentioned designs of the background art. Specifically, the spikes allow integration into the vertebral body, e.g., with relatively small spikes, without damaging the vertebral bodies. This is particularly important if future prosthetic or fusions need to be performed at that level. The cervical plates are inserted sequentially with a novel cervical plate insertion gun. The advantage of the cervical plate insertion gun is that the method of implantation is quick and efficient. No disc space distraction is needed and hence there is no fear of damaging or disarticulating posterior cervical facets. It can also be placed into narrower spaces without distraction. The mobile core of the present application also more closely approximates the natural semi-constrained motion of a healthy disc more so than the above mentioned discs.

Additional advantages of our posterior placed total lumbar artificial disc (PTTLAD) lumbar disc design have been fully reviewed in our co-pending patents, each of which have been incorporated by reference herein. The present lumbar disc plate inserter design offers two additional advantages over previous embodiments. First, the inserter design grasps the plates more securely. In addition, the sequential placement of the different plates allows placement of posterior artificial discs into narrower disc spaces.

In one general aspect, an artificial spinal disc includes a pair of substantially parallel plates formed to occupy a space defined by vertebral endplates. Each of the plates including a plurality of spikes on a first surface and a concave trough formed on a second surface opposite of the first surface. A mobile core includes a core rim with opposing convex surfaces extending from opposite sides of the core rim, the mobile core being capable of being disposed between the pair of plates to permit the vertebral endplates to move relative to one another. The spikes on each of the plates extend substantially away from the mobile core and the convex surfaces are formed to integrally fit within the concave trough of at least one of the plates. The core rim limits lateral movement of the mobile core relative to the parallel plates.

Implementations of this aspect may include one or more of the following features. For example, the plates and mobile core can be sized and shaped to integrally fit within a space defined by cervical vertebral endplates and/or lumbar vertebral endplates. Each trough can be disposed in a center of each respective, parallel plate. The troughs can be shaped to receive the convex surfaces of the mobile core and the core rim can be shaped to receive outer edges of the troughs with an integral fit. The substantially parallel plates can include a plurality of conically shaped spikes.

The mobile core rim may include at least a first substantially ring shaped member having a raised edge and a second substantially ring shaped member having a raised edge. The first and second ring shaped members may each define respective cavities where the convex surfaces are respectively positioned within and extend from. The plates can comprise an elliptical shape.

In another general aspect, an artificial disc insertion system includes an artificial disc having a pair of substantially parallel plates formed to occupy a space defined by vertebral endplates, each of the plates including a plurality of spikes on a first surface and a concave trough formed on a second surface opposite of the first surface. The disc includes a mobile core having a core rim with opposing convex surfaces extending from opposite sides of the core rim, the mobile core being capable of being disposed between the pair of plates to permit the vertebral endplates to move relative to one another. The spikes on each of the plates extend substantially away from the mobile core and the convex surfaces are formed to integrally fit within the concave trough of at least one of the plates. The core rim limits lateral movement of the mobile core relative to the parallel plates. The system also includes a surgical tool.

The surgical tool for inserting the artificial disc between vertebral endplates, the tool includes a handle portion having a trigger, an upper disc plate release button, and a lower disc plate release button. The surgical tool also includes an insertion portion extending distally away from the handle portion, the insertion portion includes an upper replacement plate releasing portion and a lower replacement plate releasing portion. The upper replacement plate releasing portion includes a release handle and a release link configured to engage and release a periphery of an upper replacement plate, e.g., to releasably secure the upper replacement plate therebetween. The lower replacement plate releasing portion includes a release handle and a release link configured to engage and release a periphery of a lower replacement plate, e.g., to releasably secure the lower replacement plate therebetween.

Implementations of this aspect may include one or more of the following features. For example, the mobile core and plates can be sized and shaped for a cervical disc replacement. The mobile core and the plates can be sized and shaped for a lumbar disc replacement. The mobile core rim may include at least a first substantially ring shaped member having a raised edge and a second substantially ring shaped member having a raised edge. The first and second ring shaped members may each define respective cavities where the convex surfaces are respectively positioned within and extend from. The plates can include an elliptical shape.

In another general aspect, a surgical tool for inserting an artificial disc between vertebral endplates includes a handle portion comprising a trigger, an upper disc plate release button, and a lower disc plate release button. The tool also includes an insertion portion extending distally away from the handle portion, the insertion portion comprising an upper replacement plate releasing portion and a lower replacement plate releasing portion. The upper replacement plate releasing portion includes a release handle and a release link configured to engage and release a periphery of an upper replacement plate, e.g., to releasably secure the upper replacement plate therebetween. The lower replacement plate releasing portion includes a release handle and a release link configured to engage a periphery of a lower replacement plate, e.g., to releasably secure the lower replacement plate therebetween.

Implementations of this aspect may include one or more of the following features. For example, the insertion portion may include an upper tip portion and a lower tip portion. The upper tip portion and the lower tip portion may be curved to facilitate posterior insertion of a lumbar replacement disc in a patient. At least one of the upper or lower replacement plate releasing portions can include a leaf spring, a tension cable and a wedge portion proximally disposed relative to the respective release handle and the release link. Each of the upper and lower replacement plate releasing portions can include a leaf spring, a tension cable and a wedge portion proximally disposed relative to the respective release handle and the release link. The tool can include a replacement disc plate driver portion for driving a replacement disc plate from a first, proximal position toward a second, distal position. The upper replacement plate releasing portion is configured to secure an upper replacement plate in a position opposite from and axially aligned with a center of a lower replacement plate held within the lower replacement releasing portion.

BRIEF DESCRIPTION OF THE DRAWINGS

FIG. 4Bi is a front view of later cervical disc bending.

FIG. 4Bii is a side view of flexion/extension cervical artificial disc motion.

FIG. 4Ci is a front view of the artificial disc showing the rotations of the mobile core between the two cervical disc plates about the x-axis (lateral bending or roll).

FIG. 4Cii is a side view of the artificial disc showing the y-axis (flexion/extension or pitch).

FIG. 4Ciii is a perspective view of the artificial disc showing the z-axis (rotation or yaw).

FIG. 7A is a view of an outside left enclosure of the cervical disc plate insertion gun.

FIG. 7B is a view of an inside left enclosure of the cervical disc plate insertion gun.

FIG. 7C is a view of an outside right enclosure of the cervical disc plate insertion gun.

FIG. 7D is a view of an inside right enclosure of the cervical disc plate insertion gun.

FIG. 8O is a view of a wedge.

DESCRIPTION OF PREFERRED EMBODIMENTS

Figure 1A:
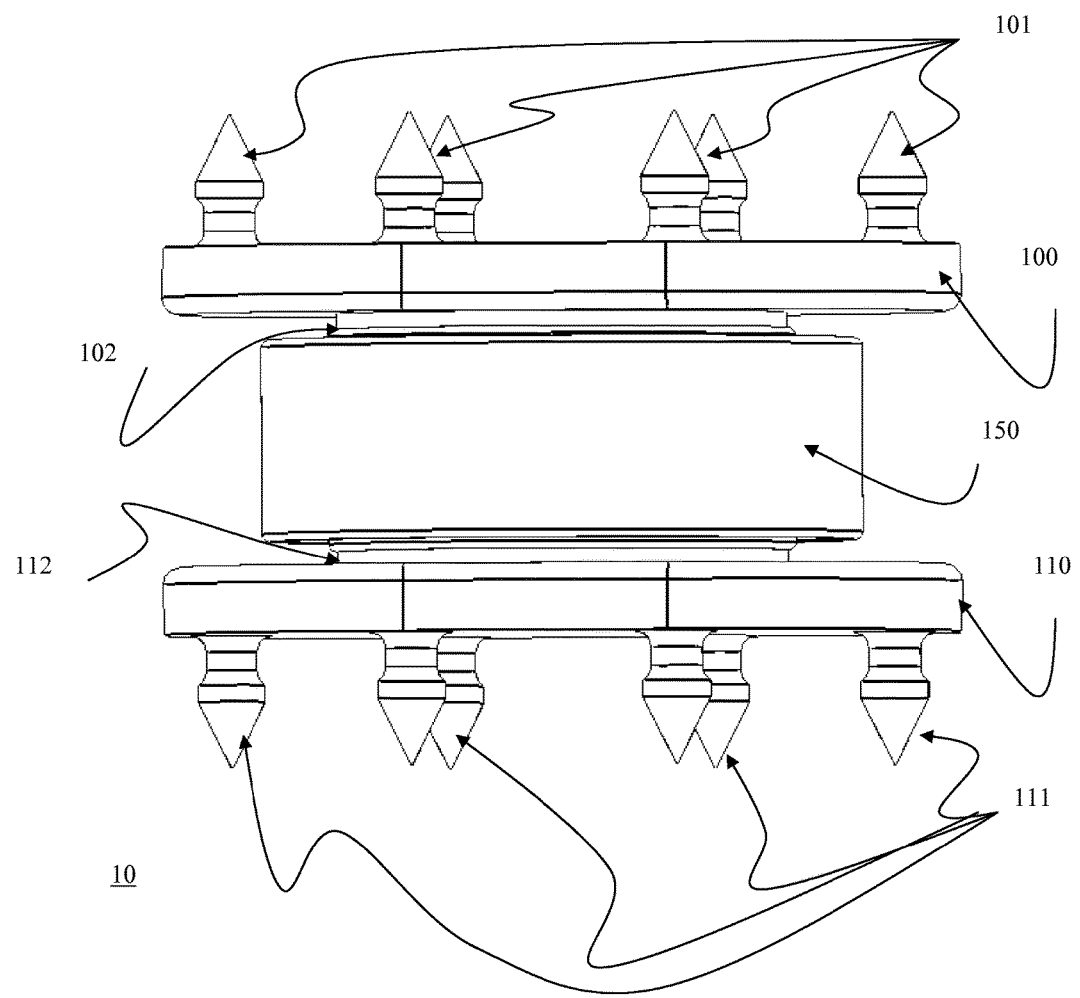
FIG. 1A is an anterior (or posterior) view of an exemplary cervical artificial disc.
Figure 1B:
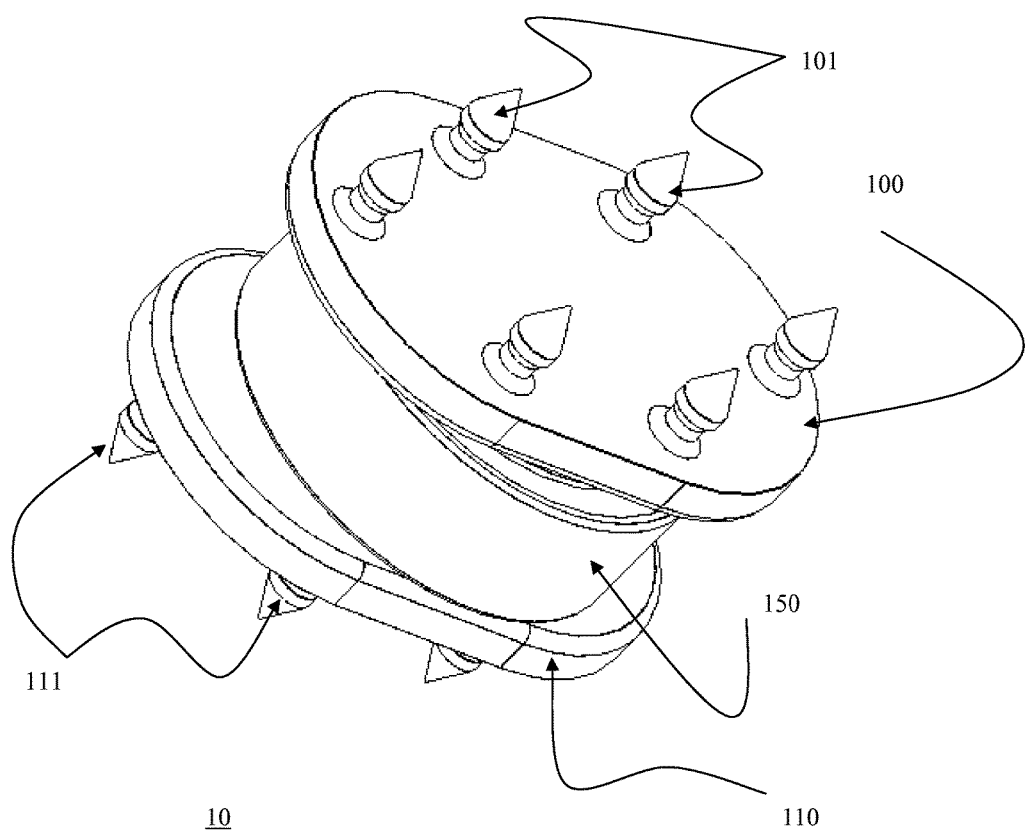
FIG. 1B is an isometric view of the cervical artificial disc of FIG. 1A.
Figure 1C:
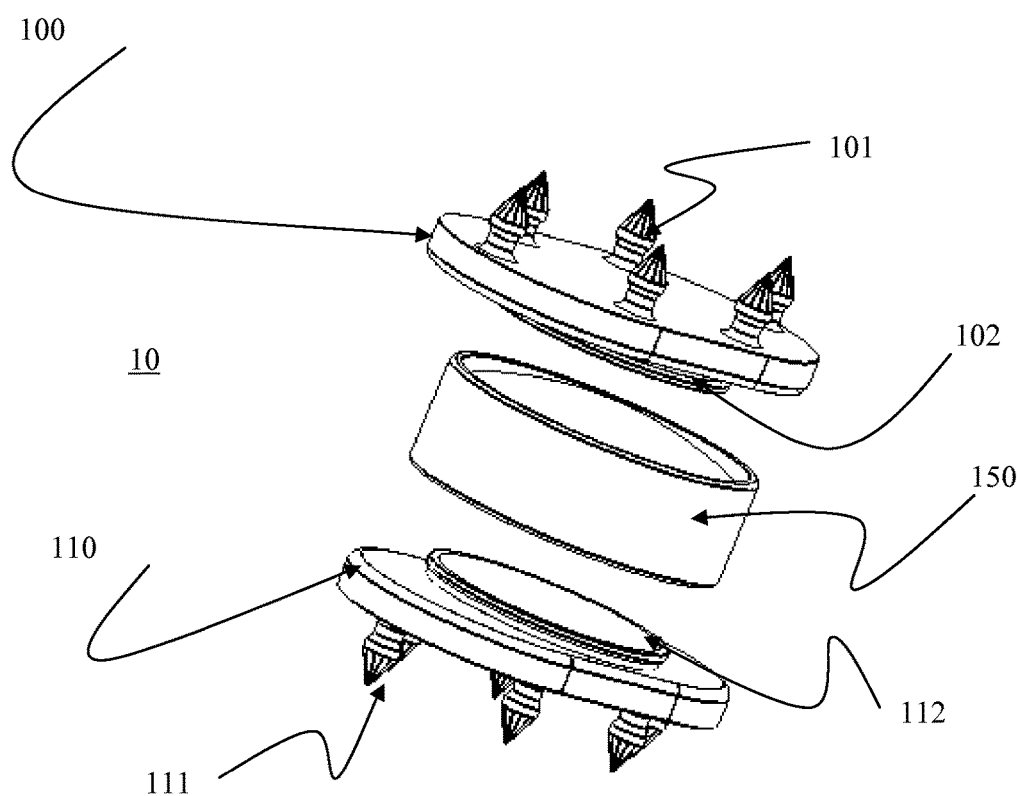
FIG. 1C is an exploded view of the cervical artificial disc of FIG. 1A.
Figure 1D:
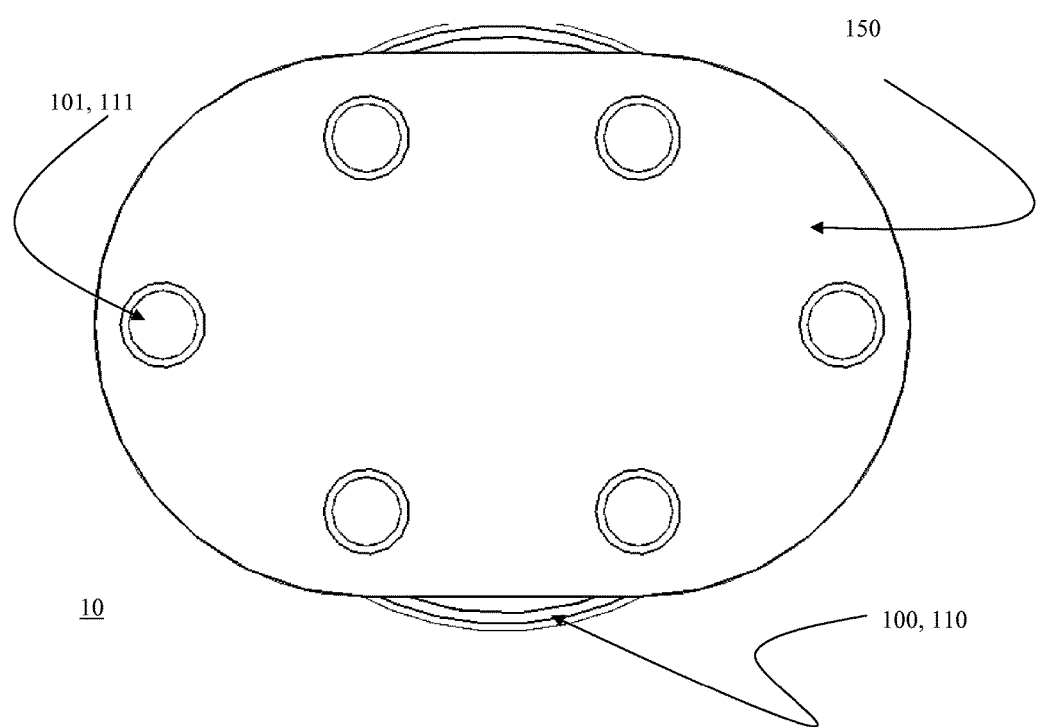
FIG. 1D is a superior (or inferior) view of the cervical artificial disc of FIG. 1A.

The Medical Device of FIG. 1-9.

Referring now to FIGS. 1-9, the above described problems of the background art can be solved in the cervical spine (and lumbar spine) after the performance of an anterior complete cervical discectomy. The disc device 10 includes an upper cervical plate 100 and lower cervical plate 110, one of which is inserted first by a plate insertion gun 500. The opposite (second) cervical disc plate 110 is then inserted with the plate insertion gun 500 maintaining parallel opposition, with opposite plates 100, 110 and troughs 102, 112 perfectly aligned. A mobile core 150 is then inserted and sandwiched in-between both cervical plates 100, 110.

FIGS. 1A-D illustrate different views of the cervical artificial disc 10. The disc 10 includes an upper plate 100 and a lower plate 110. Each plate has a plurality of spikes 101, 111, e.g., six spikes 101, 111 on each plate in a preferred embodiment, on an outer surface of the respective plate, and a centralized trough 102, 112 on an inner surface of each plate 100, 110.

Figure 2A:
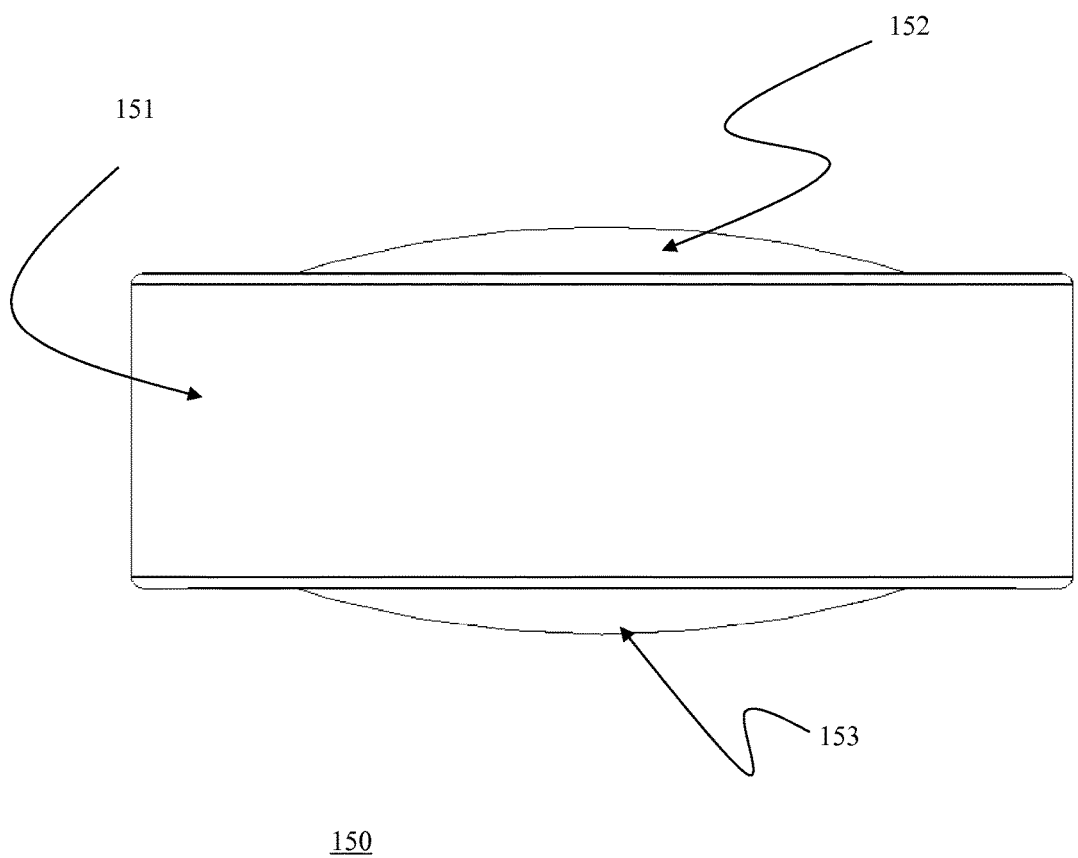
FIG. 2A is a side view of an exemplary cervical artificial disc mobile core.
Figure 2B:
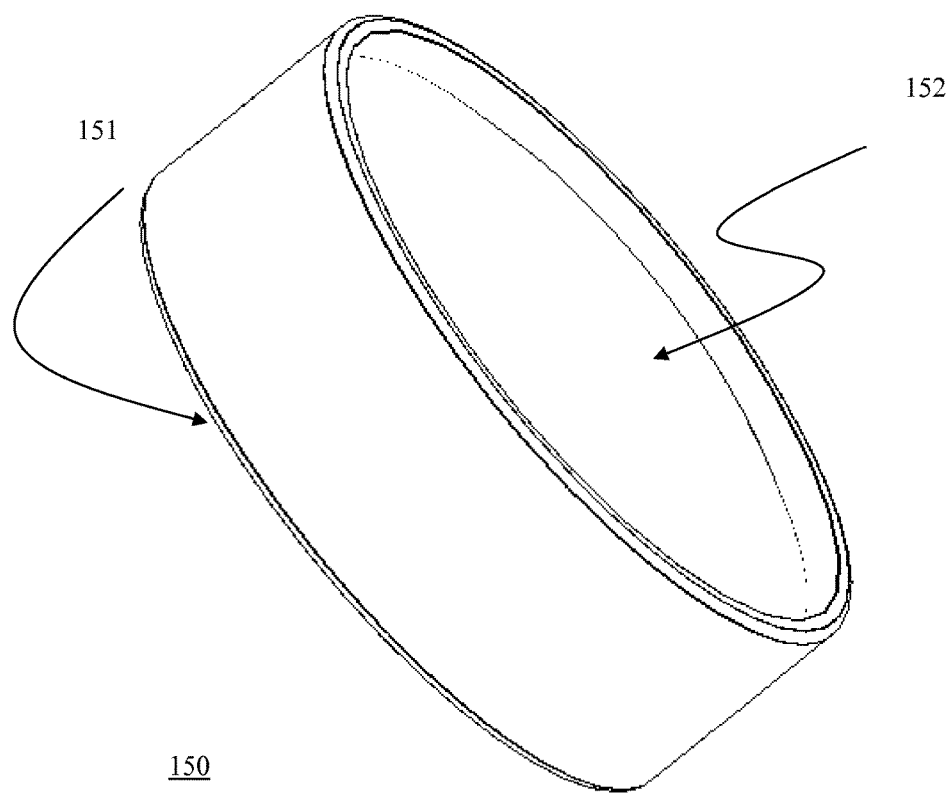
FIG. 2B is an isometric view of the exemplary cervical artificial disc mobile core.
Figure 2C:
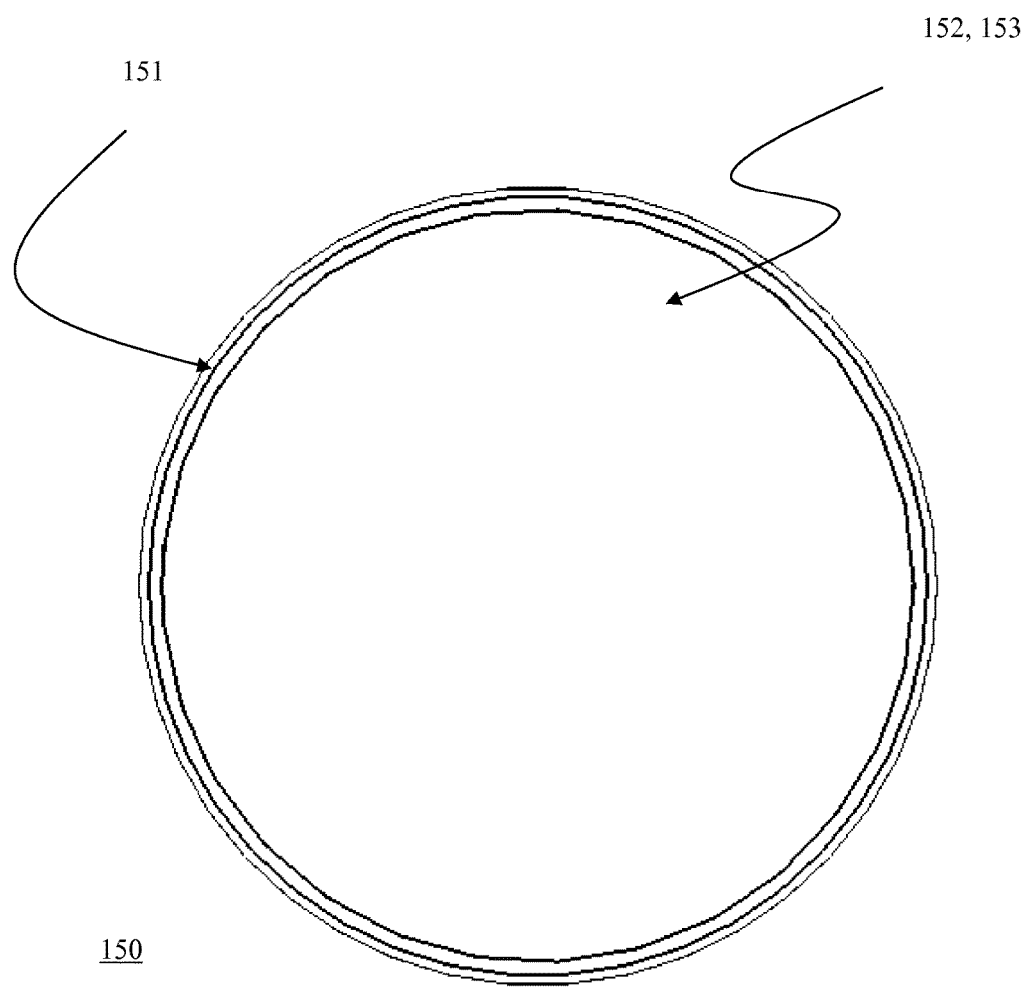
FIG. 2C is a front (or back) view of the exemplary cervical artificial disc mobile core.
Figure 3A:
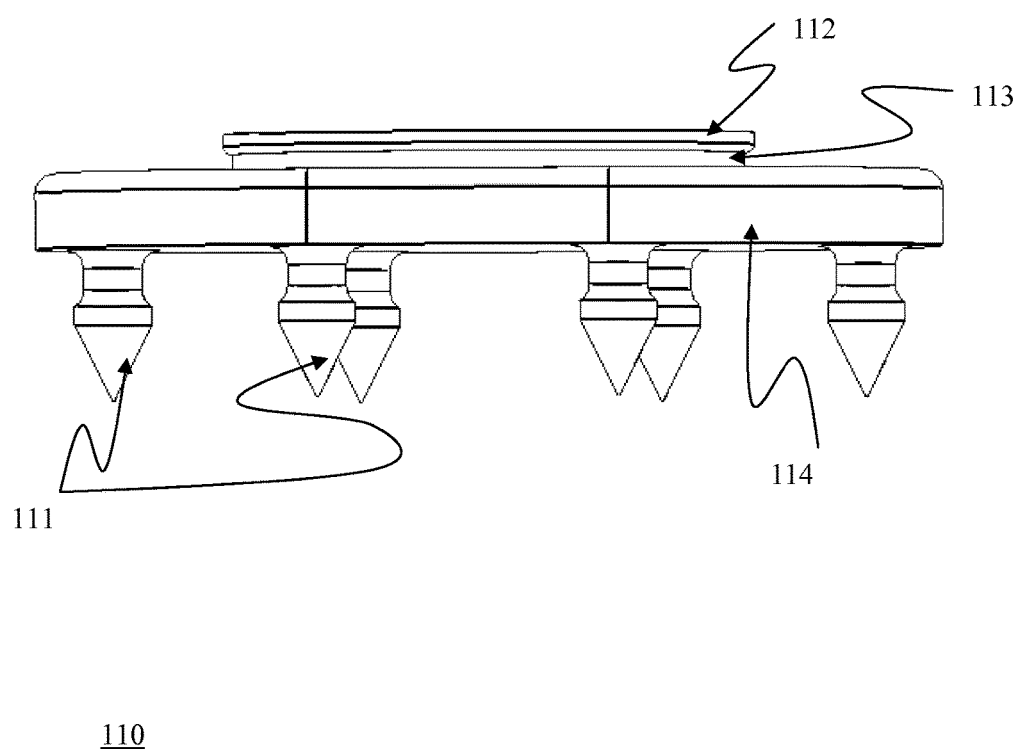
FIG. 3A is a side view of an exemplary cervical artificial disc superior or inferior plate.
Figure 3B:
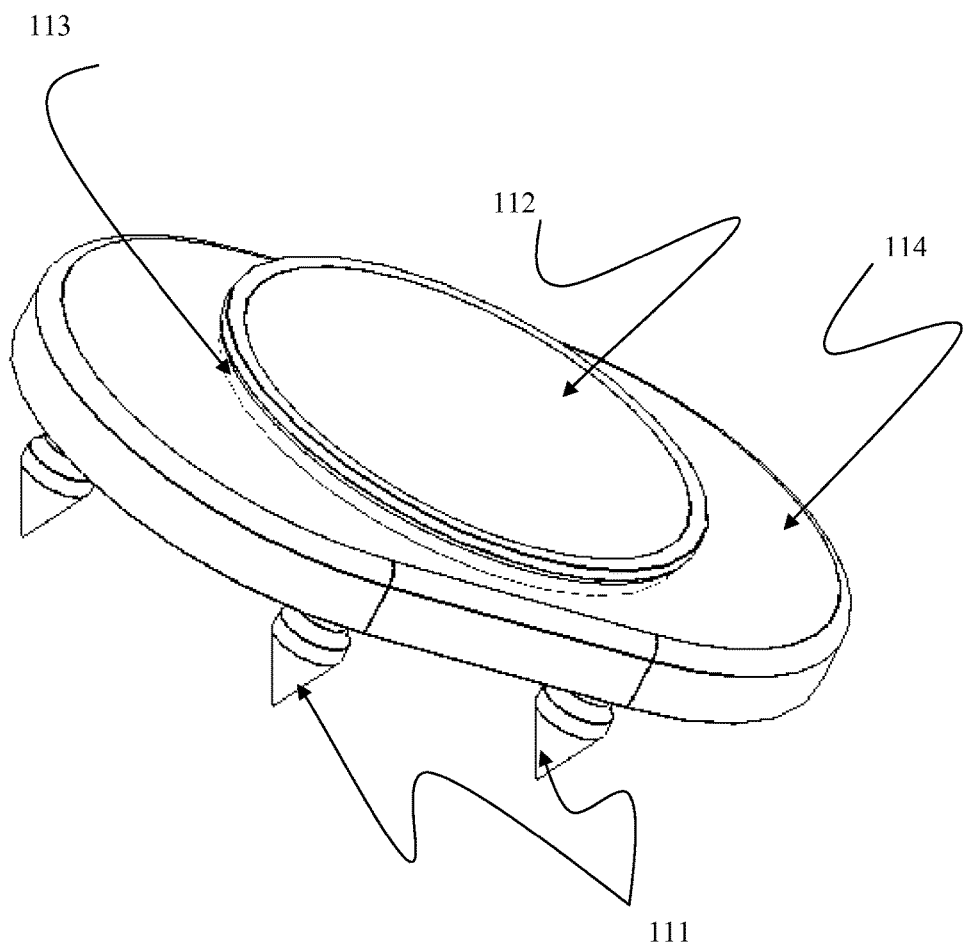
FIG. 3B is a top oblique-trough side view of the exemplary cervical artificial disc superior or inferior plate.
Figure 3C:
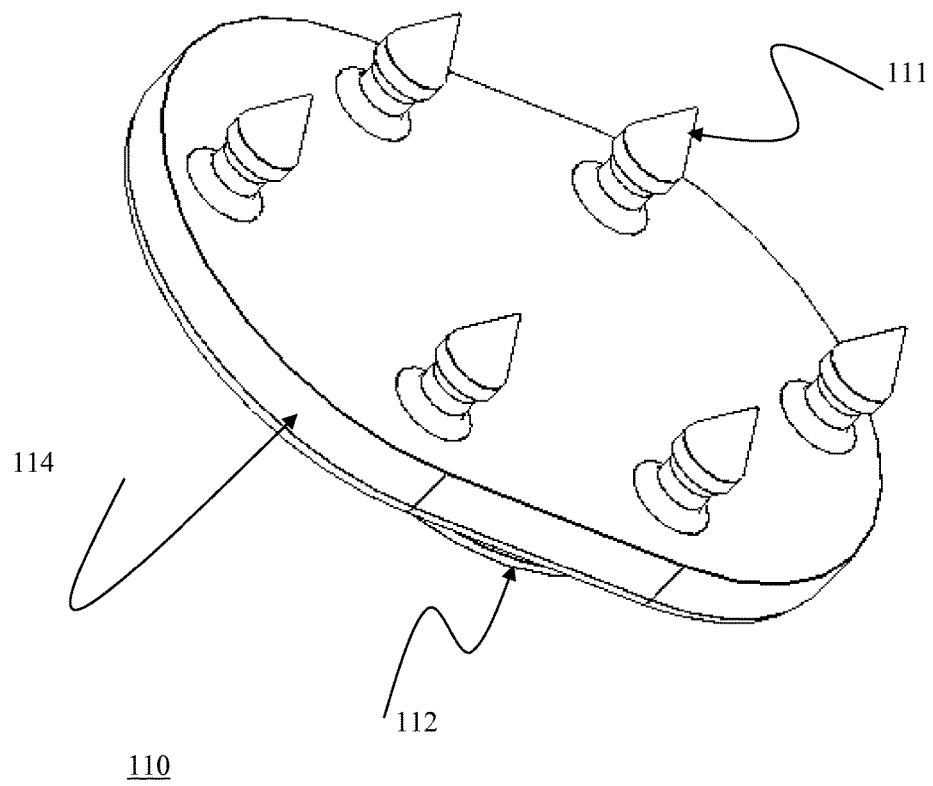
FIG. 3C is a top oblique-spike view of the exemplary cervical artificial disc superior or inferior plate.
Figure 3D:
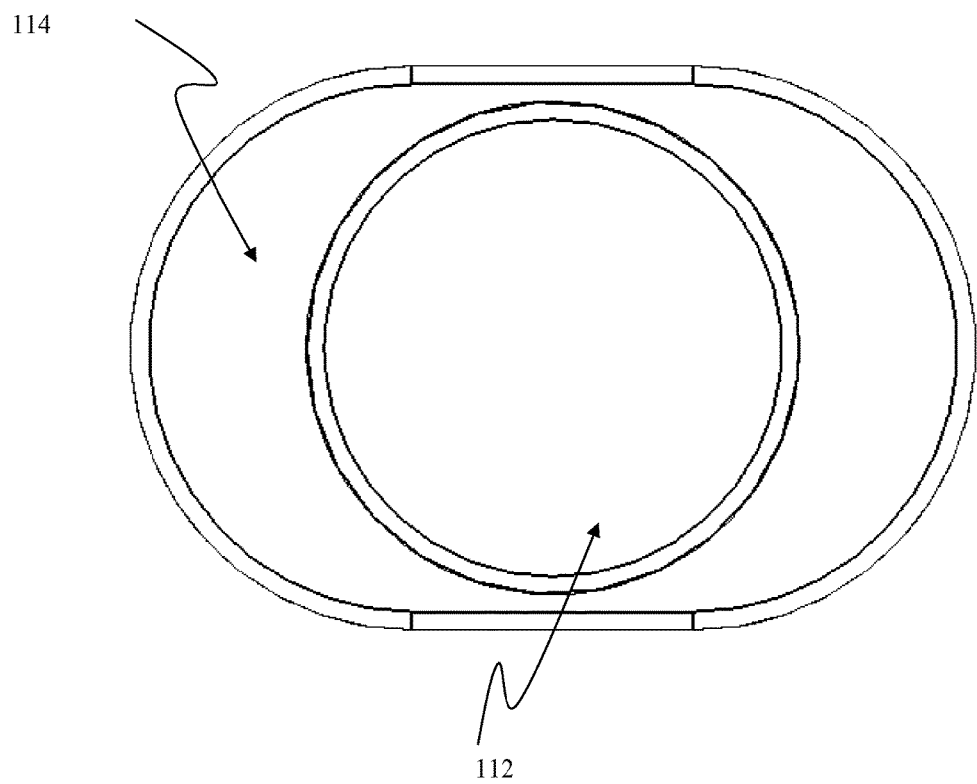
FIG. 3D is a front-trough side view of the exemplary cervical artificial disc superior or inferior plate.
Figure 3E:
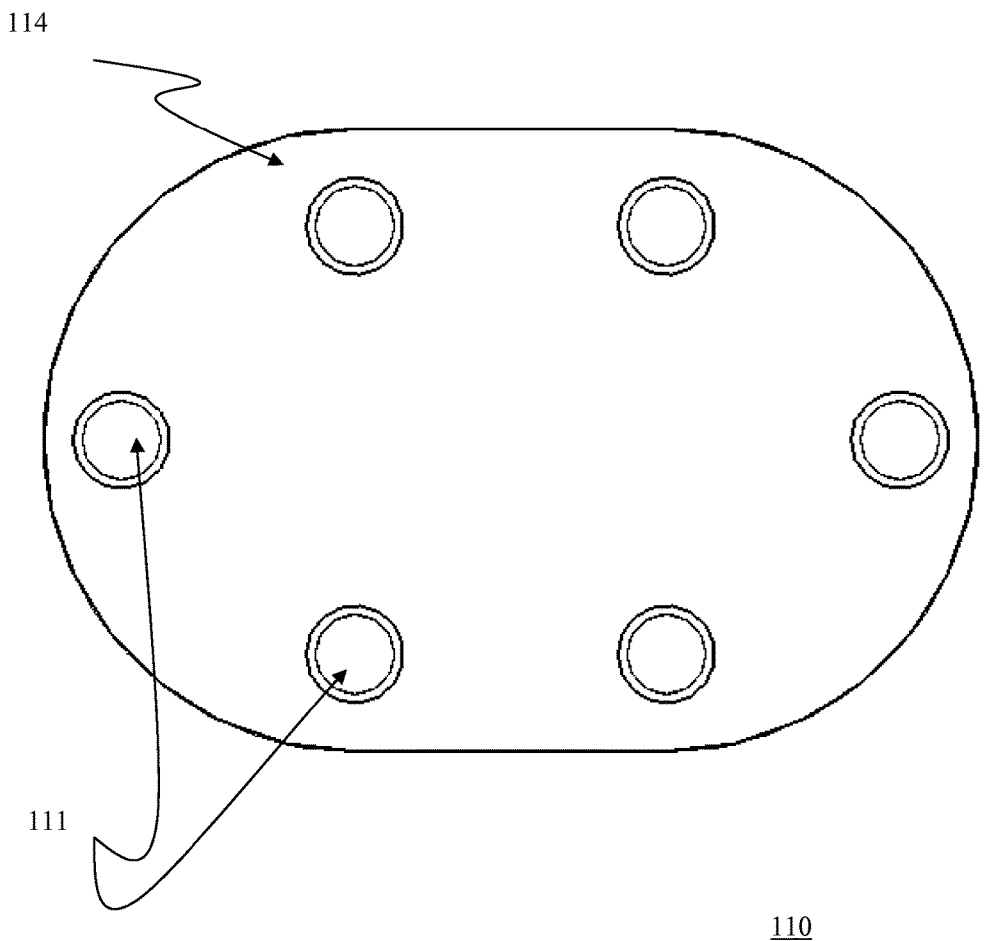
FIG. 3E is a front-spike side view of the exemplary cervical artificial disc superior or inferior plate.

FIGS. 2A-C illustrate different views of the cervical mobile core 150. The core 150 has a centralized base rim 151 with a superior convexity 152 which interacts with the trough 102 of the upper plate 100, and an inferior convexity 153 which interacts with the trough 112 of the lower plate 110.

FIGS. 3A-E illustrate different views of the cervical plate (superior or inferior) 100 (110). The plate 100 includes a base 114. On an upper surface of the inferior plate 110 is a trough 112. On a lower surface of the inferior plate 110 are 6 peripherally arranged spikes 111. The position of the trough 112 and spikes 111 are reversed for the superior plate (100). A groove 113 is defined by the trough 112 (102) and base 114 (104) of each plate 110 (100).

Figure 4A:
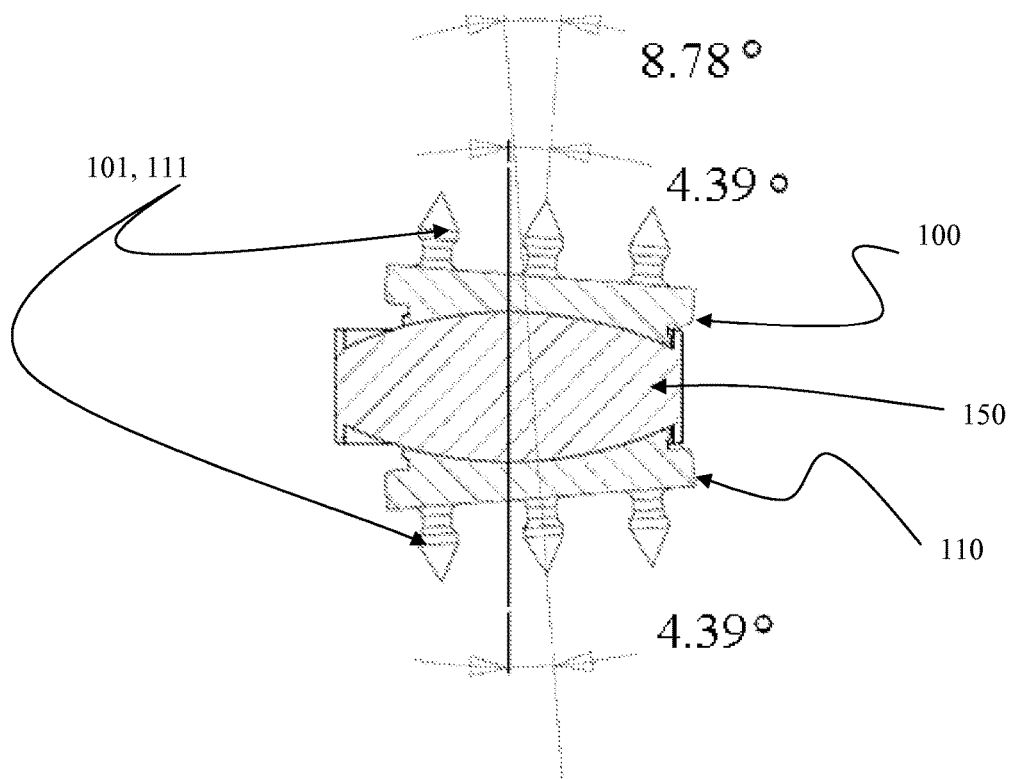
FIG. 4A is a cross-sectional view of a cervical disc core showing the angular movements about the x-axis of the cervical disc core with respect to the upper and lower cervical plates (lateral bending).

FIG. 4A illustrates a cross-sectional view of the cervical artificial disc 10 and the degrees of motion of the mobile core 150 movement about the x-axis with respect to the upper plate 100 and lower plate 110. Each disc plate 100 can bend about the x axis by 4.39 degrees clockwise and counter-clockwise (lateral bending). This means that a disc plate 100, 110 can move − or +8.78 degrees with respect to the opposite plate 110, 100.

FIG. 4B illustrates a front view of lateral bending of the artificial disc 10 (FIG. 4Bi), and a side view illustrating flexion-extension of the cervical disc 10 about the y axis which is 4.39 degrees in either flexion or extension.

FIG. 4C illustrates the rotation of the mobile core 150 between two cervical plates 100, 110 about the x (FIG. 4Ci), y (FIG. 4Cii) and z (FIG. 4Ciii) axes. Rotation about the x-axis is referred to as roll (alpha) which is lateral bending. Rotation about the y axis is referred to as pitch (Beta) which is flexion/extension. Rotation about the z axis is referred to as yaw (gamma) which is axial rotation. These figures display different views that show a reference frame for the disc assembly 10 with an origin O at the center of the core 150. The axes of rotation pass through the spherical face of the core 150 which is lower than 0 but are parallel to both the x and y axes. The rotation of the disc plates 100, 110 about the z-axis is constrained only by the spine motions once the disc 10 is implanted.

Figure 5A:
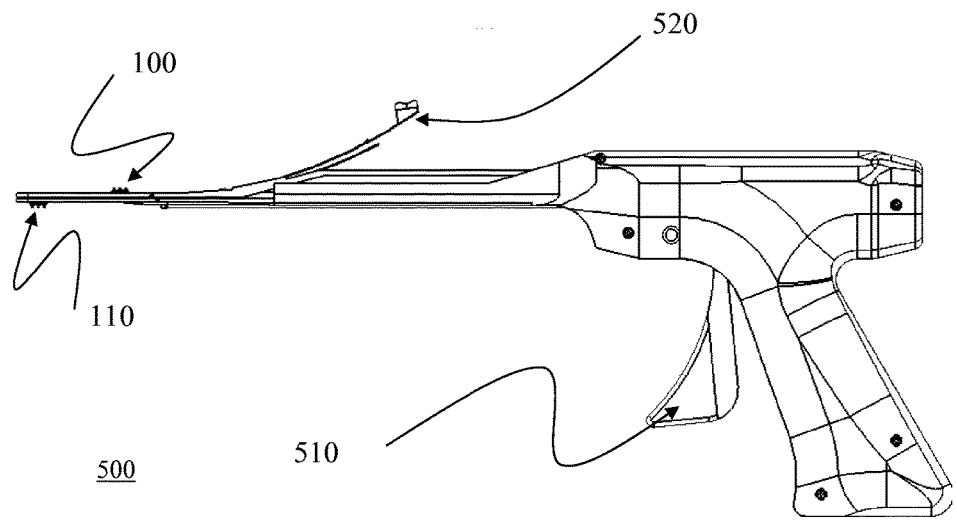
FIG. 5A is a front view of a cervical disc plate insertion gun.
Figure 5B:
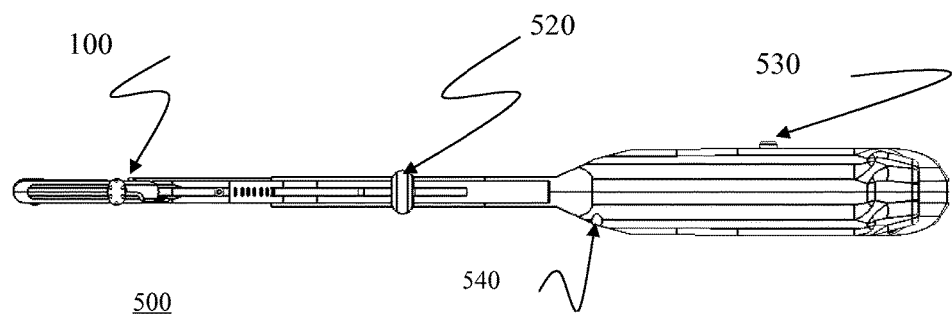
FIG. 5B is a top view of the cervical disc plate insertion gun.
Figure 5C:
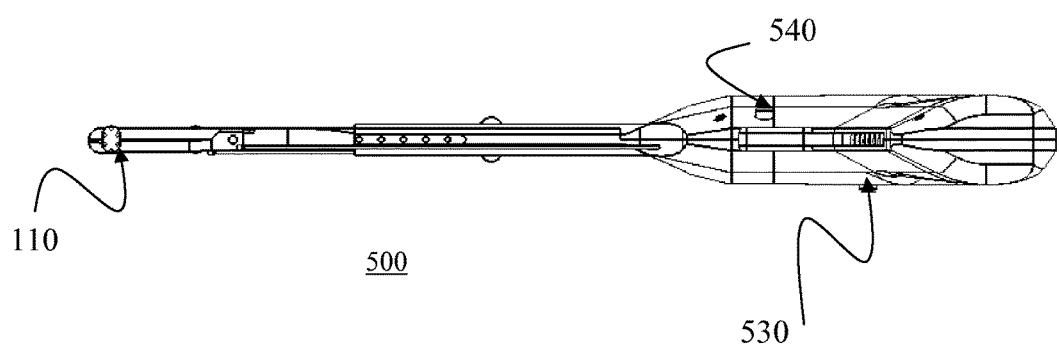
FIG. 5C is a bottom view of the cervical disc plate insertion gun.

FIGS. 5-8 illustrate the components of the cervical disc plate insertion gun 500. Various opening mechanism functions will be described in greater detail hereinafter with respect to FIGS. 5-8. The handle 512 of the opening mechanism is made up of left and right enclosures 501, 502 (FIGS. 5, 6, and 7). FIG. 7 illustrates the inside and outside aspects of left and right enclosures 501, 502. These enclosures 501, 502 are held together by five enclosure fastening screws 590 (FIG. 6B). The handle 512 holds the mechanism used to insert the upper disc plate 100 and lower disc plate 110 (FIGS. 5-6, and FIG. 8) into the vertebrae. The mechanism has two functions, including: 1) Holding onto the disc plates 100, 110 until the user releases them, and 2) opening the tip 560 and forcing one disc plate at a time into a vertebra.

1. Holding onto the Discs Until User Releases them

The mechanism has two tips 565, 580 each holding a disc plate 100, 110. The lower tip 580 is composed of two parts: the lower insertion release link 576 and the lower insertion release handle 551 (FIGS. 6 and 8). The upper tip 565 includes two parts: the upper insertion handle 550 and the upper insertion link 575 (FIGS. 6 and 8). Each tip 565, 580 works like a "lobster claw" that holds a disc plate by the "groove" 552 on its cylindrical extrusion. When the tip 565, 580 is closed the two opposing parts e.g. the lower insertion release link 576 and the lower insertion release handle 551 (FIGS. 6 and 8) hold a disc plate 110 firmly.

Figure 6A:
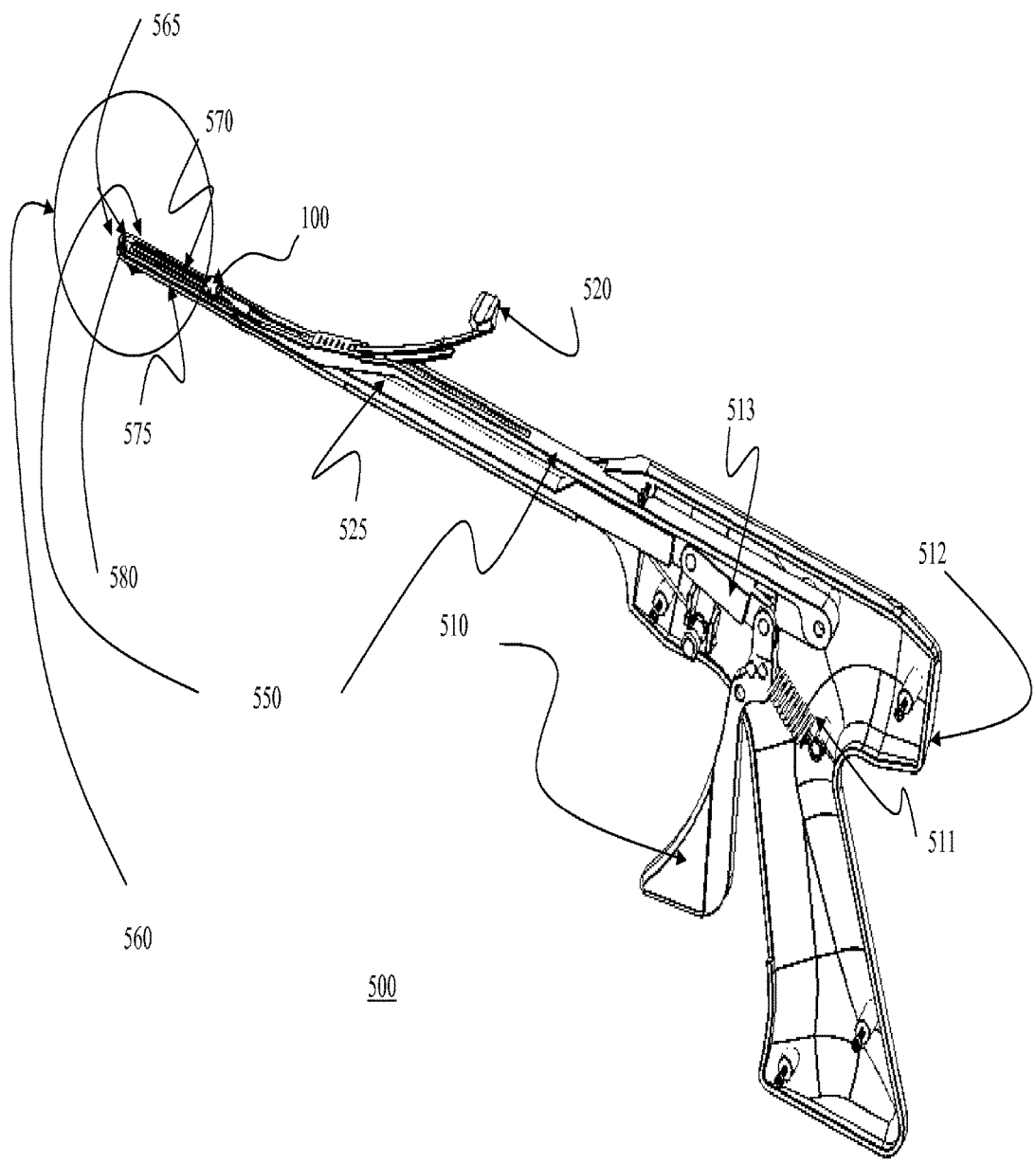
FIG. 6A is a perspective, left-side, cut-away view of the cervical disc plate insertion gun.
Figure 6B:
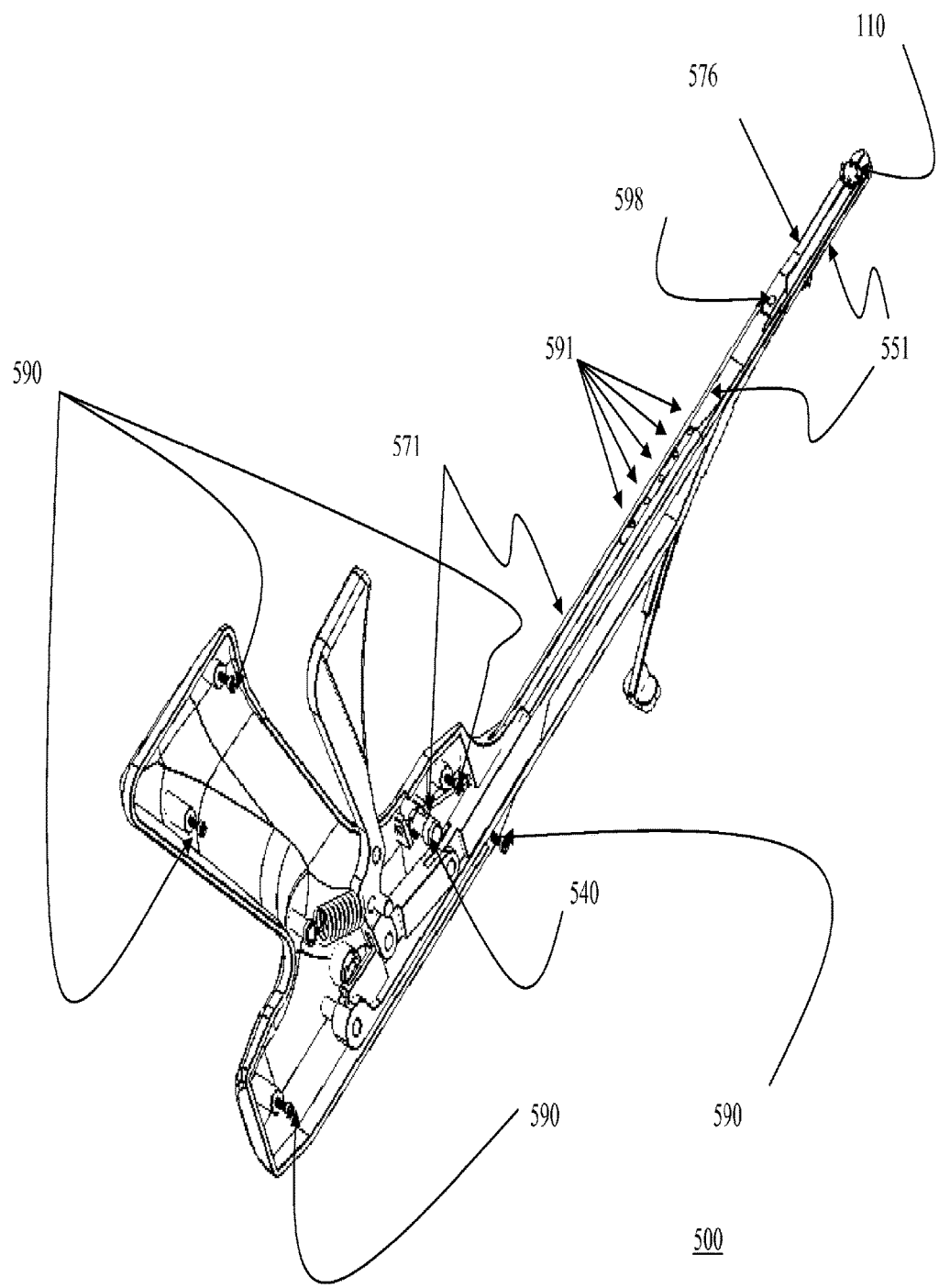
FIG. 6B is a left side, bottom angle view of the cervical disc plate insertion gun.
Figure 6C:
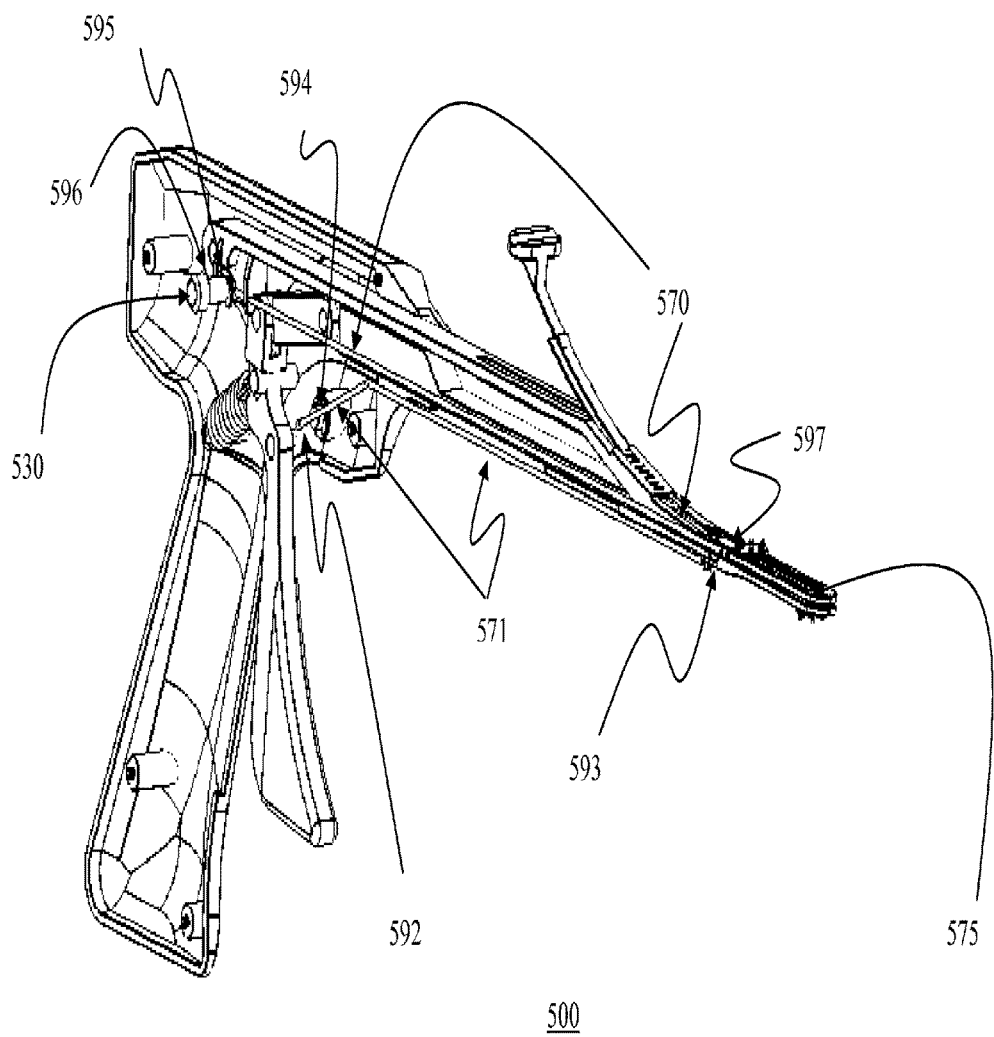
FIG. 6C is a right side, top angle view of the cervical disc plate insertion gun.
Figure 6D:
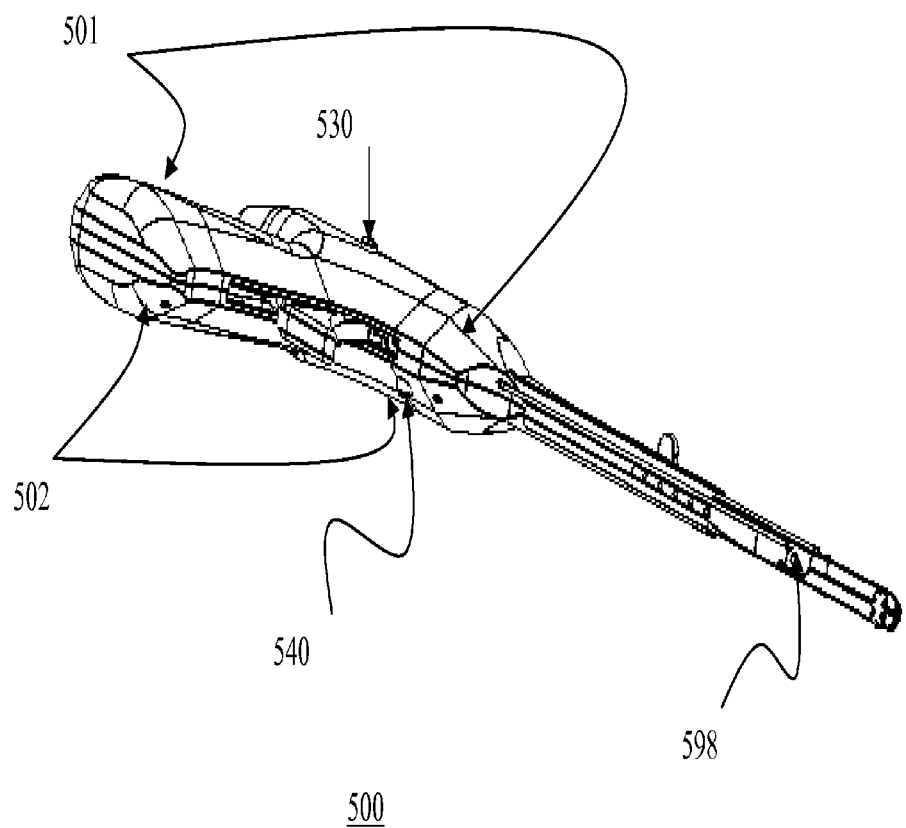
FIG. 6D is a right side, bottom angle view of the cervical disc plate insertion gun.
Figure 6E:
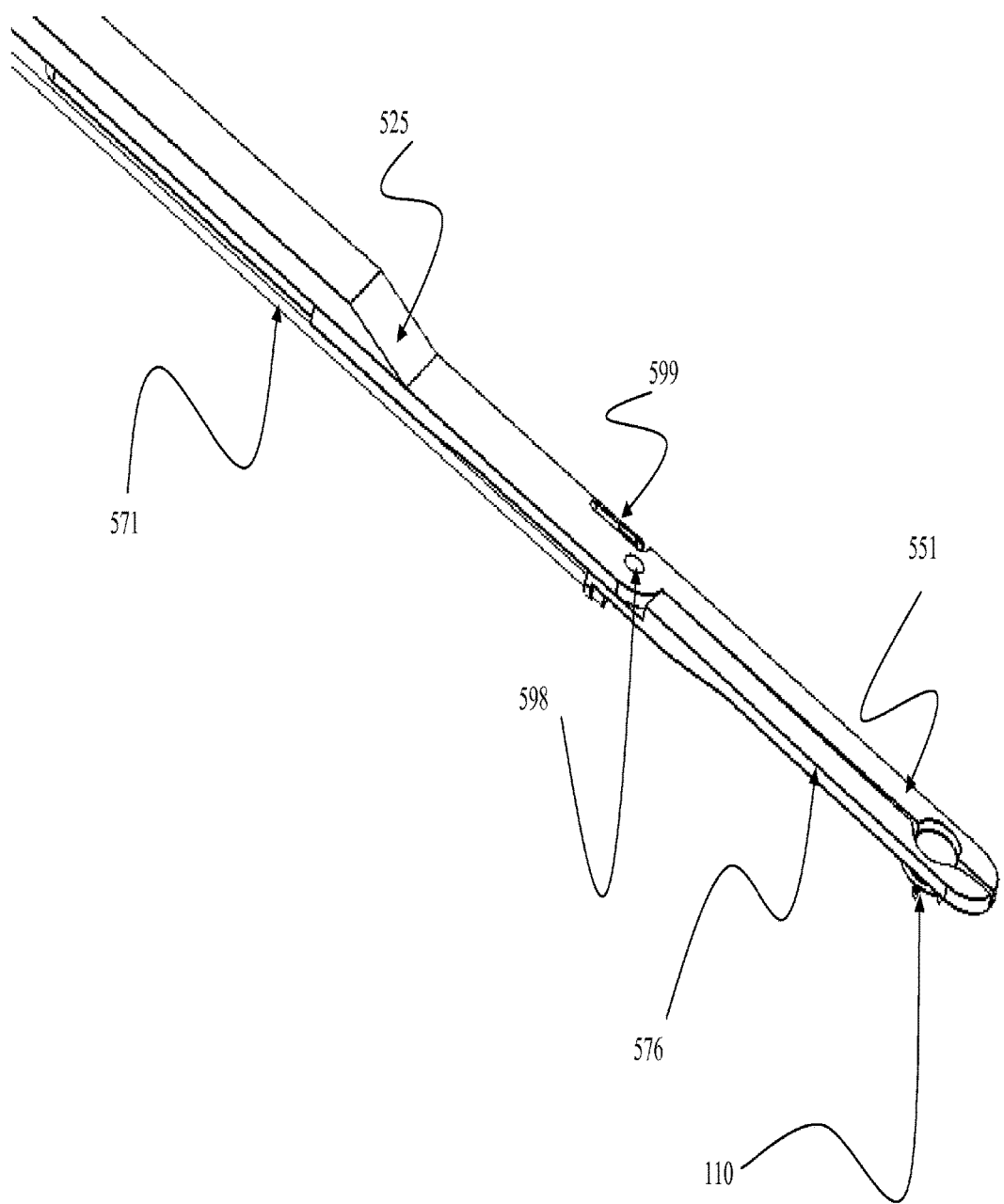
FIG. 6E is a cut-away view of the tool tip lower cervical disc replacement plate release mechanism.
Figure 8A:
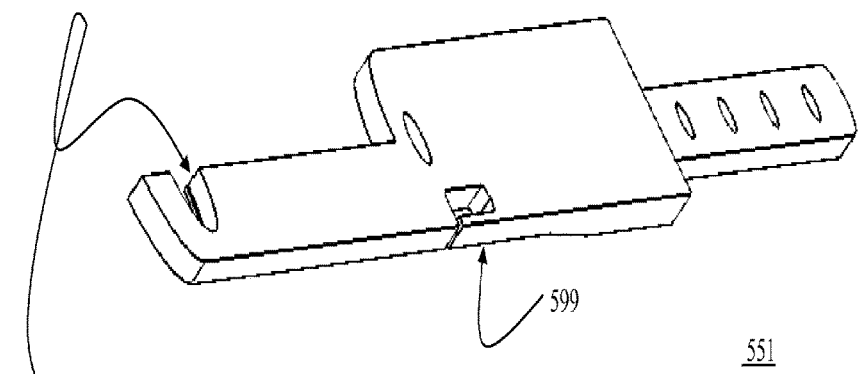
FIG. 8A is a top view of inner components of the cervical plate insertion gun including the lower insertion handle.
Figure 8B:
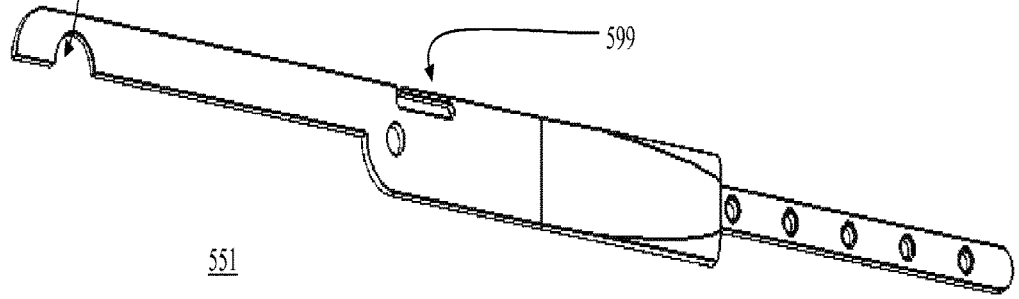
FIG. 8B is a lower insertion handle bottom view.
Figure 8C:
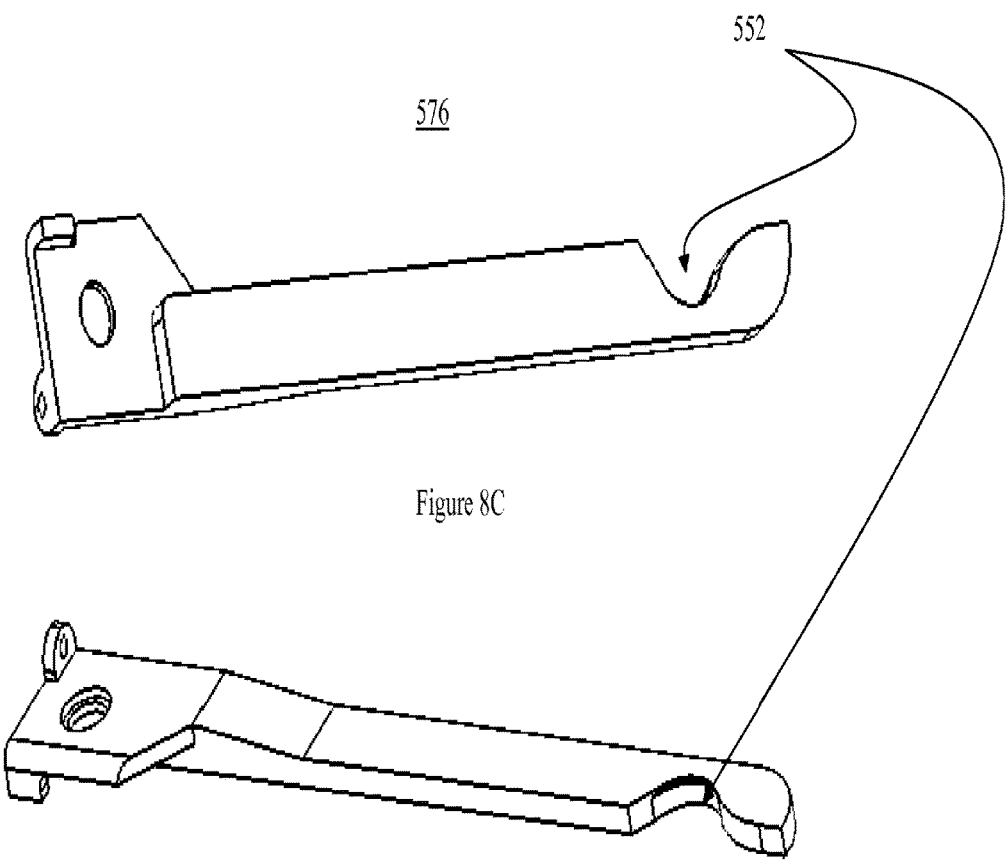
FIG. 8C is top view of a lower insertion link.
Figure 8D:
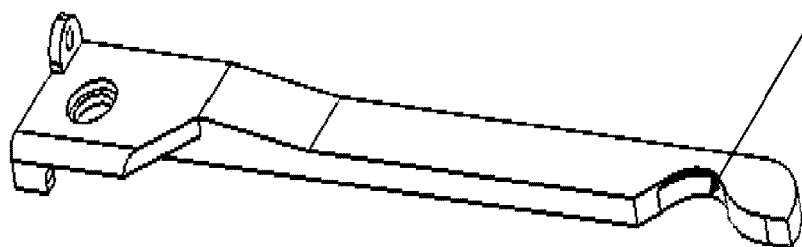
FIG. 8D is bottom view of the lower insertion link.
Figure 8E:
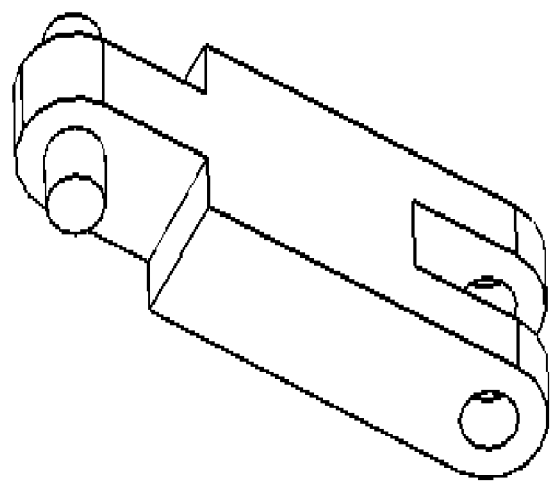
FIG. 8E is a view of the wedge link.
Figure 8F:
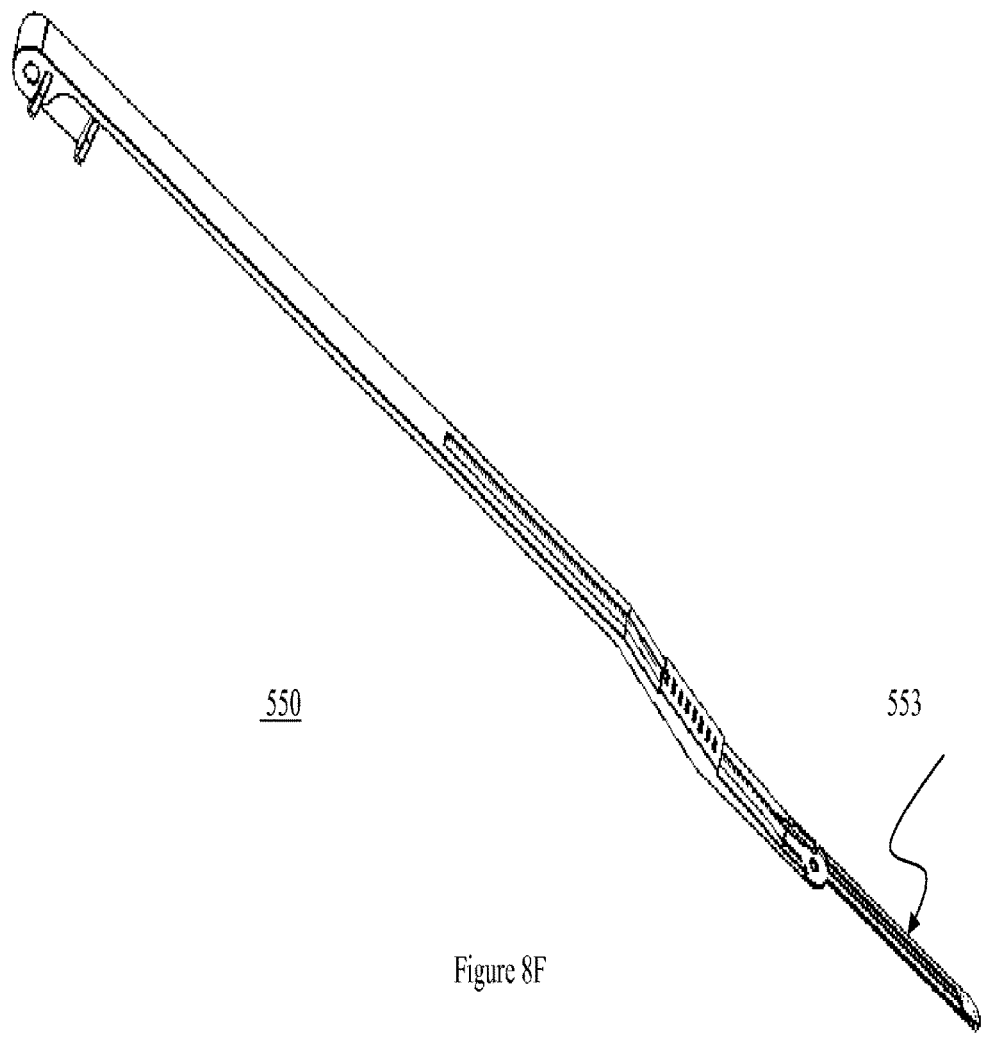
FIG. 8F is a top view of the upper insertion handle.
Figure 8G:
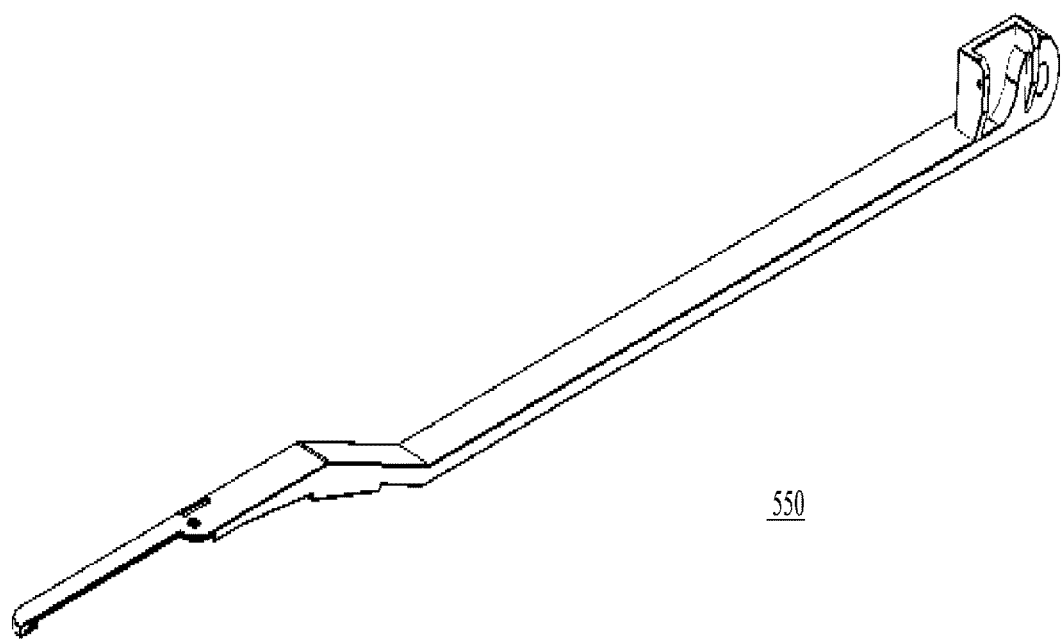
FIG. 8G is a lower view of the upper insertion handle lower view.
Figure 8H:
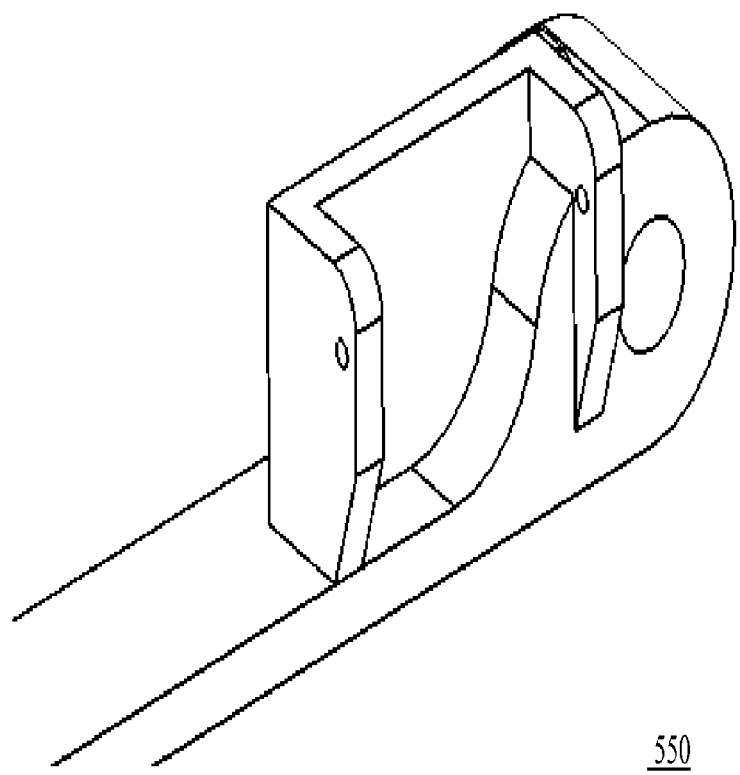
FIG. 8H is a close-up bottom view of a rear portion of the upper insertion handle.
Figure 8I:
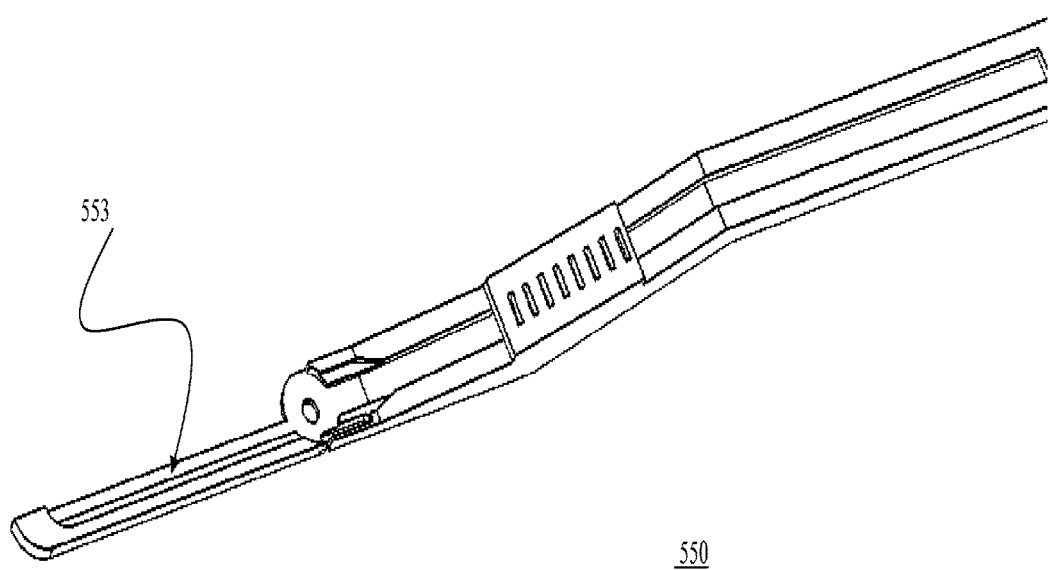
FIG. 8I is a close-up, top view of a forward portion of the upper insertion handle.
Figure 8J:
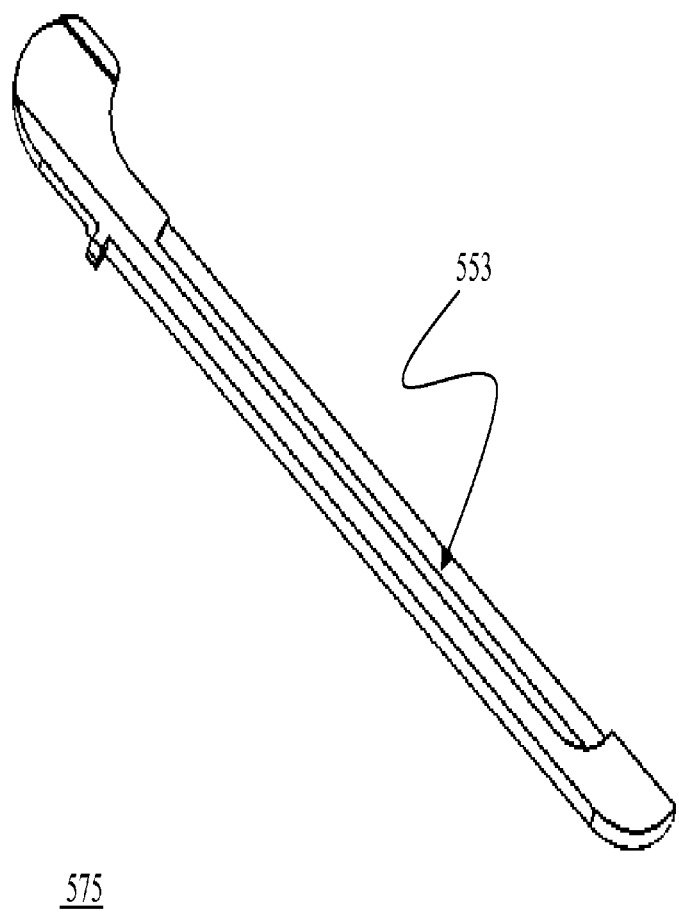
FIG. 8J is a top view from left of the upper insertion release link.
Figure 8K:
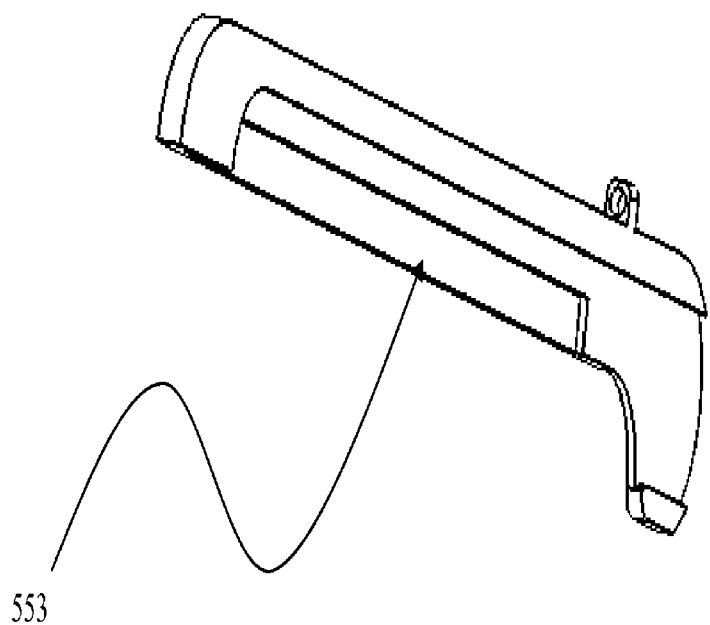
FIG. 8K is a top view from a right side of the upper insertion link.
Figure 8L:
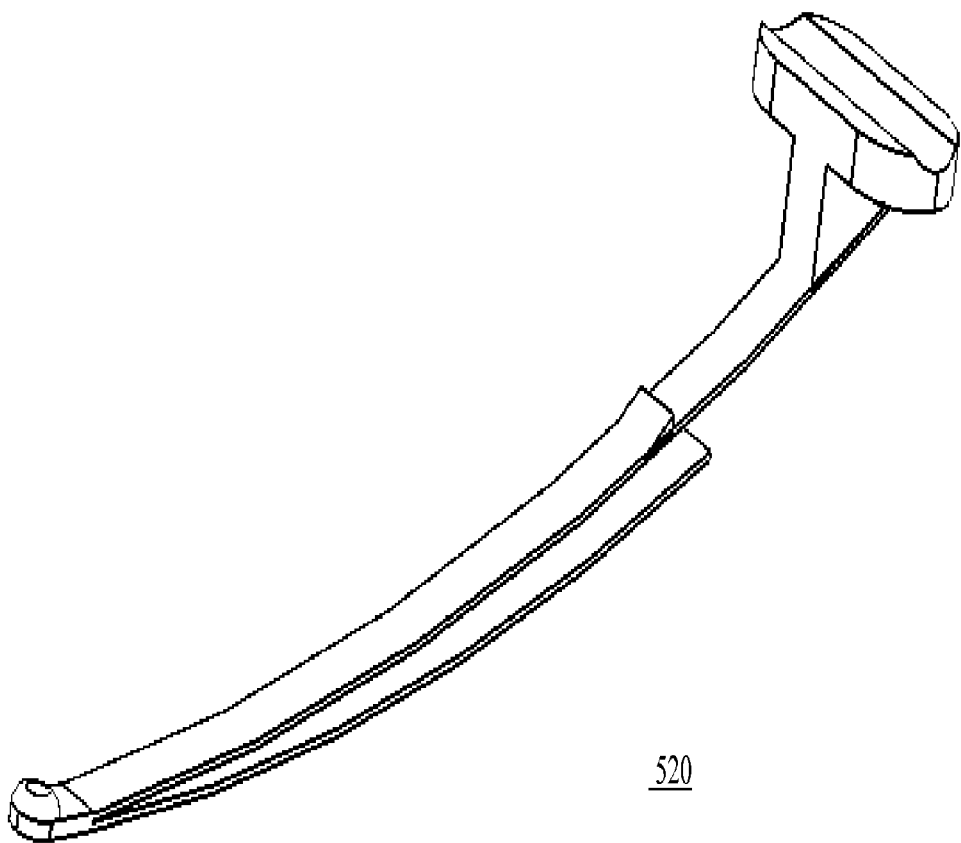
FIG. 8L is a view of a manual upper disc replacement plate driver.
Figure 8M:
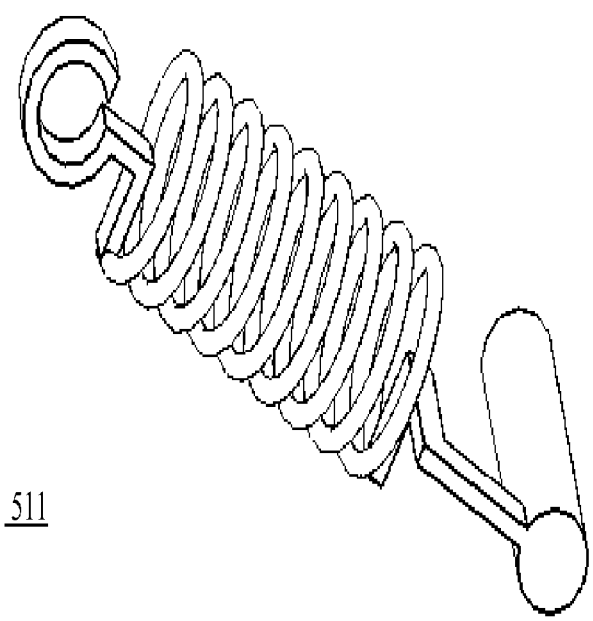
FIG. 8M is a view of a trigger spring.
Figure 8N:
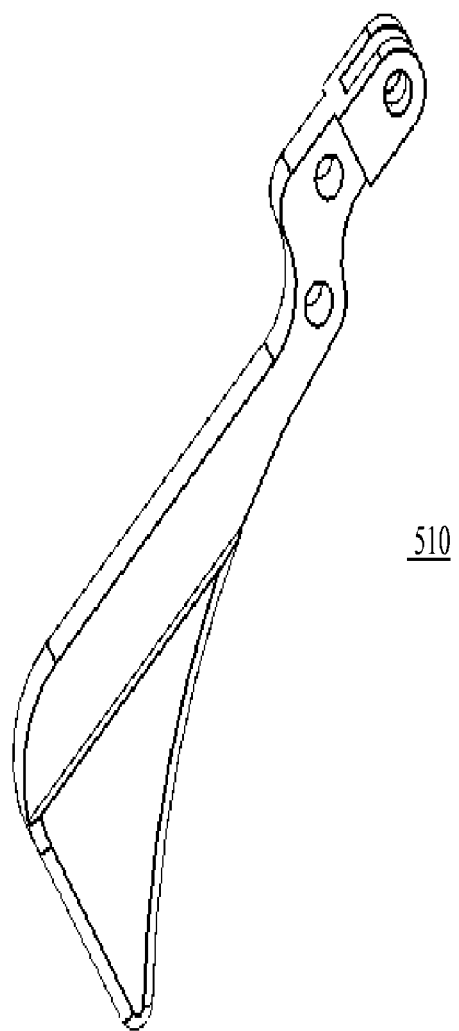
FIG. 8N is a view of a trigger.
Figure 80:
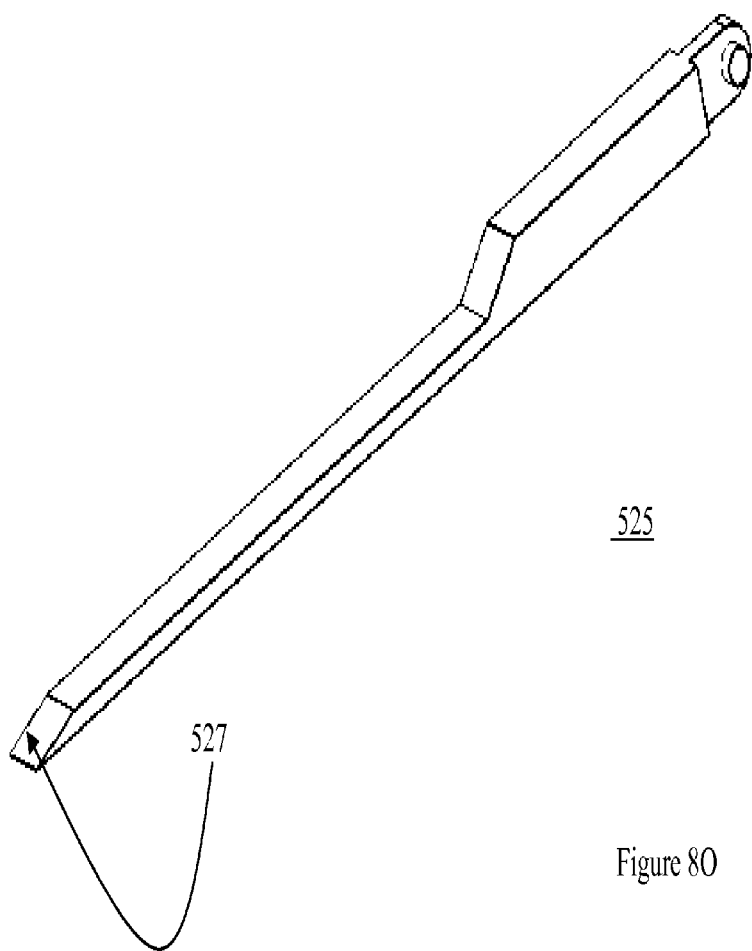

A tip 580 opens to release a disc plate as follows. A lower tension cable 571 pulls on the lower insertion release link 576 (FIGS. 6 and 8) that pivots about the lower release pin 598 (FIG. 6) and opens up a gap big enough to loosen the grip on the disc groove 552. The lower tension cable 571 (FIG. 6) can only exert a tensile force to open the lobster claw 580. The natural state of the lobster claw 580 is to be closed. This is ensured by pre-loading the lower insertion release link 576 with the help of a leaf spring 599 cut into the lower insertion release handle 551 (FIGS. 6E and 8). The lower tension cable 571 pulls on the lower insertion release link 576 (FIGS. 6 and 8) each time the user presses on the lower release button 540. The lower tension cable 571 is clamped on one end by a lower rear crimp 592 (FIGS. 6 and 8). Hence when the lower release button 540 is pressed, the tension on the lower tension cable 571 increases (in the same way the tension of a guitar string increase when one presses on the string with a finger). The tension then pulls the lower insertion release link 576 forcing it to swing open. When the user lets go of the button 540, the tension disappears and the spring 599 carved in the lower insertion release handle 551 forces the lower insertion release link 576 to swing closed (FIG. 6E).

The upper tip 565 works in a similar fashion except that its opening is triggered by the upper release button 530.

2. Opening its Tip and Forcing One Disc at a Time into a Vertebra

The mechanism tips 565, 580 open each time the user presses on trigger 510. When the trigger 510 rotates, it pushes on the wedge link 513 which in turn pushes on the wedge part 525 (FIG. 8). The wedge part 525 is wedged at its front action end that creates a gap in between the lower tool tip 580 and upper tool tip 565 forcing them to open.

A typical disc insertion operation starts with a lower disc plate 110 placed in the lower tip 580 and the opposing upper disc plate 100 placed on the upper side but away from the tip 565 (as shown in FIGS. 5,6, and 8). A channel 553 along the upper tip 565 that is formed by the upper insertion release handle 550 and the upper insertion release link 575 which holds the second disc plate 100 in place and serves to guide it to the tip 565 when needed.

Once the tool tip 560 is inserted into the inter-vertebral space, the first disc plate 100 is inserted into the lower vertebra by opening the tool tip 560. To keep alignment, the lower tool tip 585, "lower lobster claw", is kept closed (FIG. 6), securing the disc plate just inserted. The tool 500 should be left in place. The second, upper, disc 100 initially placed in the upper tool half, away from the "upper lobster claw" 565 but away from the tip is then slid down to the end of the upper lobster claw 565 by a flexible and manually activated upper disc replacement plate driver 520 (FIGS. 6 and 8). Once the second disc 100 is positioned at the tip of the upper "lobster claw" 565 (FIG. 6), the tool tip 560 is opened once more, i.e., the upper tip 565 and lower lobster claw tip 580 are separated from each other, by virtue of the wedge 525 that is activated by the trigger 510, via wedge link 513 action. Once the second, upper, disc plate 100 is inserted, the user can press on the upper release button 530 and lower release button 540 to release both discs (by opening the upper and lower "lobster claws" 565, 580) and at the same time close the tool tip 560 (by releasing the trigger 510). The tool tip 560 then closes while both "lobster claws" 565, 580 remain open, leaving both disc plates 100, 110 in place. The tool tip 560 can then be removed from the patient and a mobile core placed in between the two aligned disc plates 100, 110.

Figure 9A:
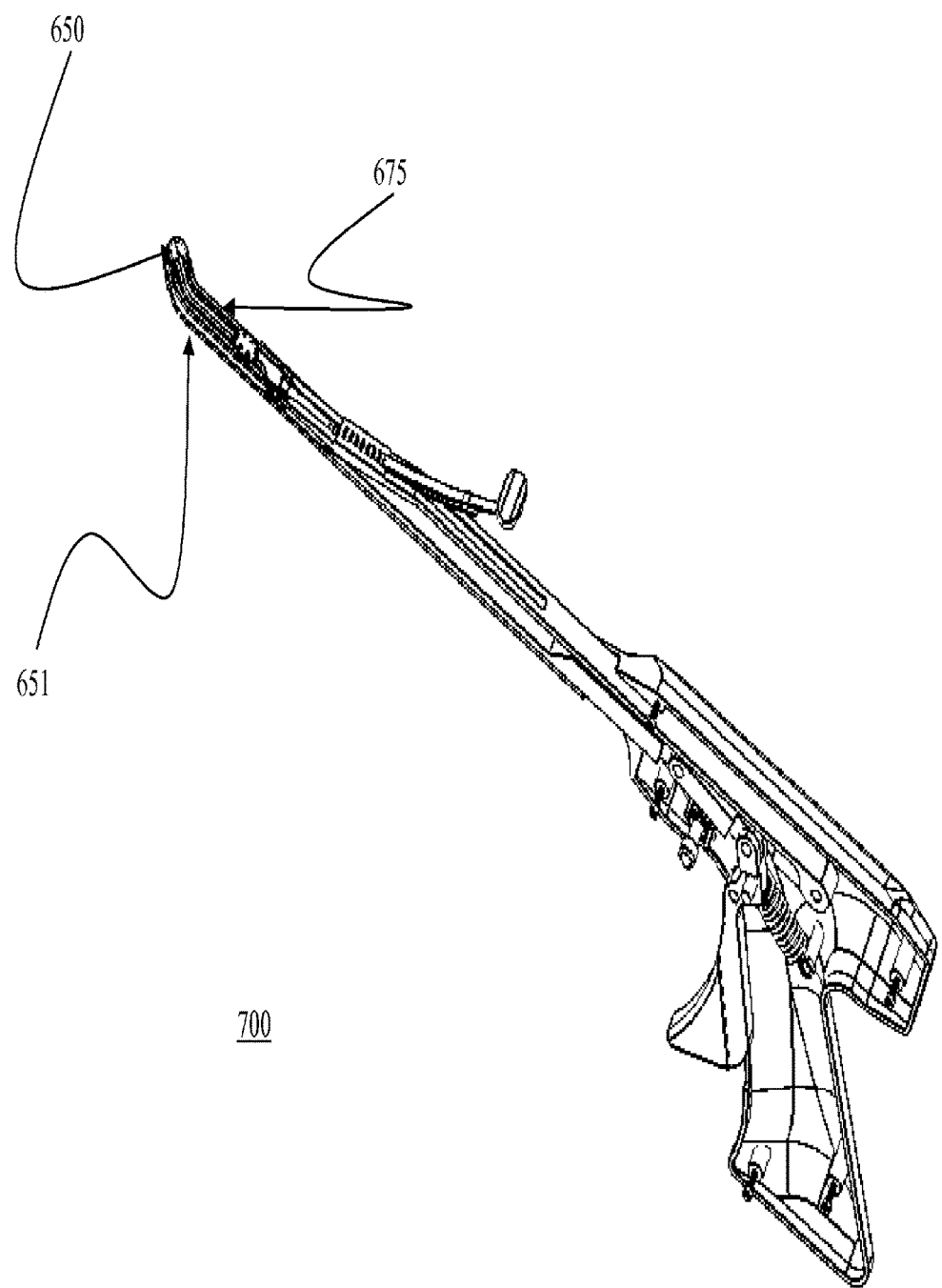
FIG. 9A is a perspective cut away view of an exemplary lumbar disc plat insertion gun.

This anterior cervical disc gun can be modified and enlarged for placement of anterior lumbar disc plates. FIG. 9A illustrates the modified posterior lumbar disc plate insertion gun 700. The gun 700 is identical to the cervical disc plate insertion gun 500 except its tips 660 are angled to allow insertion of the specifically sized lumbar disc plates 100, 110 in the posterior lumbar spine underneath the thecal sac.

Figure 9B:
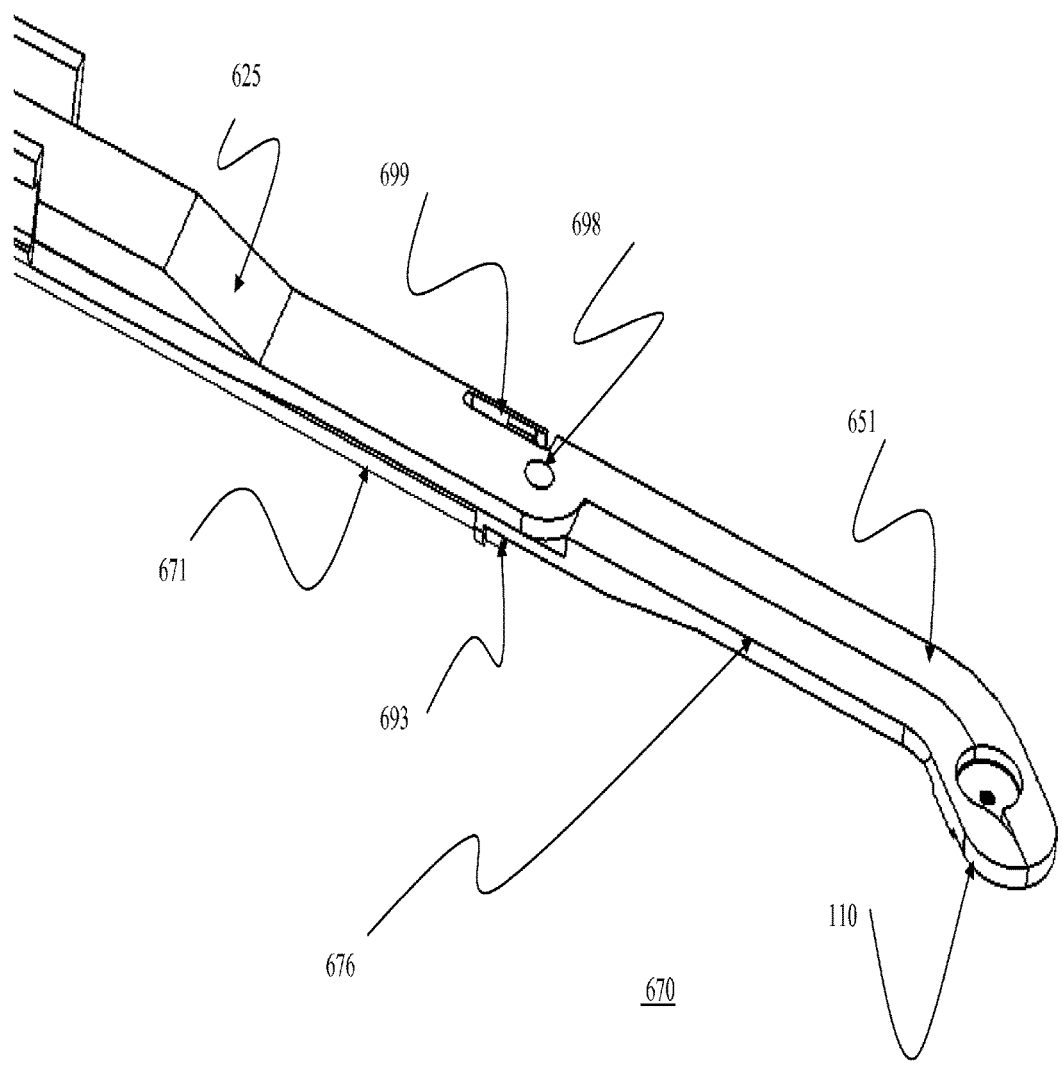
FIG. 9B is a cut-away view of the tool tip of the lower lumbar disc replacement plate release mechanism.

FIG. 9B illustrates an enlarged cut-away view of the tool tip 660 of the lumbar lower disc replacement plate release mechanism 670. The mechanism 670 is identical to that described for the cervical mechanism which is illustrated FIG. 6E. The tips 660 of the lumbar tool are however, specifically designed and adapted for the typically bean shaped lumbar disc plates.

The Surgical Method

The method of insertion of the cervical artificial disc (or lumbar artificial disc) into the anterior cervical spine can be performed open microscopically, or closed tubularly, using endoscopic and/or fluoroscopic guidance.

After the adequate induction of anesthesia the patient is positioned in the supine position. Routine exposure of the anterior cervical spine is performed and the appropriate disc space is radiographically identified and exposed. A routine complete anterior cervical discectomy is performed.

The cervical disc plates are inserted onto the cervical disc plate insertion gun 500. The tips 560 of the gun 500 are placed into the intervertebral space. Fluoroscopy is used to assure centrality of disc plate placement.

The trigger 510 of the gun 500 is depressed and the bottom plate 110 is inserted into the lower vertebrae. Once this penetrates the bone, the lower plate releasing button 540 is depressed, thereby releasing the plate from the inserter claws 580 (FIG. 6E). The second upper plate 100 is now manually driven into the space by the gun's manual plate driver 520. Because of the design of the gun 500, the upper plate 100 is perfectly aligned with the lower plate 110. The gun trigger 510 is depressed and this drives the upper plate 100 into the upper vertebrae. The upper plate releasing button 530 is now depressed, releasing the upper plate 100 from the inserter lobster claws 565. The gun 500 is removed from the interspace. A mobile core 150 of the appropriate height is selected and placed in between the upper and lower cervical disc plates 100, 110, respectively. The patient is closed routinely.

The surgical method for the posterior insertion of the PPLTAD into the posterior lumbar interspace can be performed open microscopically, or closed tubularly, using endoscopic and or fluoroscopic guidance.

After the adequate induction of anesthesia the patient is positioned in the prone position. A midline incision is made, the appropriate unilateral lamina is radiographically identified and exposed, and a unilateral hemi-laminotomy is performed preserving facet stability. A complete discectomy is performed, and the superior and inferior endplates are exposed. The lumbar plate insertion gun 700 is placed underneath the thecal sac. Fluoroscopic guidance may be used to verify centrality of lumbar disc plate placement. The trigger of the gun 700 is depressed which leads to insertion of the lower lumbar disc plate 100 into the lower vertebra. The lower lumbar disc plate releasing button is depressed which releases the plate from the inserter claws 551 (FIG. 9B). The second upper plate 100 is now manually driven into the interspace by the gun's 700 manual plate driver (520). Because of the design of the gun mechanism as described above, the second plate 100 is now perfectly aligned with the first lumbar disc plate 110. The gun trigger is depressed, and this drives the upper plate 100 into the upper vertebrae. The upper lumbar disc plate release button is now depressed and this releases the upper lumbar disc plate from the claws of the inserter gun 700. The gun 700 is removed from the space. An appropriately sized mobile core 150 is now inserted in between upper and lower lumbar disc plates 100, 110. The patient is closed routinely.

The current device allows safe placement of lumbar and cervical artificial discs into the spine without intervertebral distraction, and therefore places minimal tension on facet joints. The method of insertion is quick, gentle, and time efficient. The plate insertion gun could potentially be adapted for other inter joint orthopedic devices, and further adaptations may have applications in manufacturing, toy, carpentry and other industries.

What is claimed is:

1. An artificial disc system comprising:
   an artificial disc comprising:
   first and second plates formed to occupy a space defined by vertebral endplates of a spine, each of the first and second plates including an endplate-engaging surface having plurality of anchors and a core-engaging surface positioned opposite the endplate-engaging surface; and
   a mobile core sized and configured to be positioned between the first and second plates to permit the first and second plates to move relative to one another, wherein the anchors on the endplate-engaging surface extend substantially away from the mobile core and the core-engaging surfaces engage first and second plate-engaging surfaces of the mobile core, wherein both of the first and second plate-engaging surface are configured to slide against adjacent core-engaging surfaces of the first and second plate and wherein at least one of the first and second plate-engaging surface of the mobile core is substantially convex such that the first plate can move with respect to the second plate about an x-axis for lateral bending, a y-axis for flexion/extension, and a z-axis for axial rotation of the spine, wherein the core-engaging surface of the first plate is substantially concave and is sized and shaped for engaging a convex portion of the first plate-engaging surface of the mobile core, wherein the plurality of anchors on the endplate-engaging surface of the first plate comprise a first group of anchors on a left side of the first plate and a second group of anchors on a right side of the first plate with a middle portion of the first plate having no anchors between the first and second groups of anchors, wherein the plurality of anchors on the endplate-engaging surface of the second plate comprise a third group of anchors on a left side of the second plate and a fourth group of anchors on a right side of the second plate with a middle portion of the second plate having no anchors between the third and fourth groups of anchors; and
   a surgical tool for inserting the artificial disc between vertebral endplates, the surgical tool comprising:
   a handle;
   an elongate insertion portion extending distally away from the handle portion; and
   an implant holder connected at a distal end of the elongate insertion portion and having a first tip sized and configured to engage the first plate and a second tip size and configured to engage the second plate so as to hold both the first and second plates relatively firmly during insertion and position of the first and second plates in the space defined by the vertebral endplates of the spine, wherein the implant holder comprises a claw having first and second curved portions that engage the first plate to hold the first plate, wherein the first curved portion of the claw is pivotable with respect to the second curved portion of the claw so as to release the first plate when the claw is opened.

2. The artificial disc system of claim 1, wherein the claw is biased to a closed position in a natural state to hold the first plate and the claw releases the first plate only in response to a force exerted to open the claw.

3. The artificial disc system of claim 1, wherein the claw comprises a spring that pre-loads the claw to bias the claw to a closed position to hold the first plate.

4. The artificial disc system of claim 3, wherein the spring comprises a leaf spring.

5. The artificial disc system of claim 1, wherein the first plate can tilt with respect to the second plate by over 8 degrees with respect to each of the x-axis and the y-axis.

6. The artificial disc system of claim 1, wherein the mobile core comprises a rim configured to engage a projecting portion on at least one of the first and second plates to limit movement of the mobile core with respect to the at least one of the first and second plates.

7. The artificial disc system of claim 1, wherein the artificial disc is sized and configured to be a cervical artificial disc to be inserted in a cervical disc space.

8. The artificial disc system of claim 1, wherein the convex portion of the first plate-engaging surface of the mobile core has a first height and a first radius with first height less than the first radius, wherein the mobile core has a radially outer portion that is positioned radially outward of the convex.

9. The artificial disc system of claim 1, wherein the mobile core has a first width along the x-axis from a core front to a core back and a second width along the y-axis from a first core side to a second core side, and wherein the second width is equal to the first width.

10. The artificial disc system of claim 1, wherein the mobile core has a first width along the x-axis from a core front to a core back and a second width along the y-axis from a first core side to a second core side, and wherein the second width is at least as great as the first width.

11. The artificial disc system of claim 1, wherein the core-engaging surfaces of both of the first and second plates have substantially curved portions, wherein both of the plate engaging surfaces of the mobile core have substantially curved portions sized and shaped to engage the substantially curved portions of the core-engaging surfaces of the first and second plates, and wherein the first tip of the implant holder is an elongate upper tip and the second tip of the implant holder is an elongate lower tip positioned below the elongate upper tip.

12. The artificial disc system of claim 11, wherein the surgical tool attaches to the first and second plates without engaging the mobile core.

13. The artificial disc system of claim 11, wherein the surgical tool comprises at least one hinge actuatable to allow for grabbing and releasing of the artificial disc and comprises a leaf spring configured to bias the surgical tool in a first position.

14. The artificial disc system of claim 11, wherein the first plate is configured to be capable of tilting with respect to the second plate by over 8 degrees with respect to each of the x-axis and the y-axis.

15. The artificial disc system of claim 11, wherein curved portion of the core-engaging surface of the first plate comprises a concave portion, wherein the core-engaging surface further comprises a substantially flat portion extending circumferentially around the concave portion of the core-engaging surface of the first plate.

16. The artificial disc system of claim 15, wherein the core-engaging surface of the first plate comprises a raised rim between the concave portion and the flat portion.

17. The artificial disc system of claim 11, wherein the artificial disc is sized and configured to be a cervical artificial disc to be inserted in a cervical disc space.

* * * * *